(12) United States Patent
Wiehe et al.

(10) Patent No.: US 9,315,510 B2
(45) Date of Patent: Apr. 19, 2016

(54) **METHOD AND APPLICATION OF UNSYMMETRICALLY *MESO*-SUBSTITUTED PORPHYRINS AND CHLORINS FOR PDT**

(75) Inventors: Arno Wiehe, Berlin (DE); Daniel Aicher, Berlin (DE); Christian B. W. Stark, Leipzig (DE); Volker Albrecht, Bergholz-Rehbruecke (DE); Susanna Gräfe, Jena (DE)

(73) Assignee: Biolitec Pharma Marketing LTD, Labuan (MY)

( * ) Notice: Subject to any disclaimer, the term of this patent is extended or adjusted under 35 U.S.C. 154(b) by 371 days.

(21) Appl. No.: 13/119,907

(22) PCT Filed: Sep. 17, 2009

(86) PCT No.: PCT/US2009/057283
§ 371 (c)(1),
(2), (4) Date: Mar. 18, 2011

(87) PCT Pub. No.: WO2010/033678
PCT Pub. Date: Mar. 25, 2010

(65) Prior Publication Data
US 2011/0206613 A1     Aug. 25, 2011

Related U.S. Application Data

(60) Provisional application No. 61/098,026, filed on Sep. 18, 2008.

(51) Int. Cl.
A61K 31/409     (2006.01)
C07D 487/22     (2006.01)
C07H 15/26      (2006.01)

(52) U.S. Cl.
CPC .............. *C07D 487/22* (2013.01); *C07H 15/26* (2013.01)

(58) Field of Classification Search
CPC .................................................... C07D 487/22
USPC ............................................. 424/9.1; 514/25
See application file for complete search history.

(56) References Cited

U.S. PATENT DOCUMENTS 5,831,088 A * 11/1998 Dolphin et al. ............... 540/474

FOREIGN PATENT DOCUMENTS

DE            10146970        *  4/2003   .......... C07D 487/22

OTHER PUBLICATIONS

Wiehe et al (Hydrophilicity vs hydrophobicity—varying the amphiphilic structure of porphyrins related to the photosensitizer m-THPC. J. Porphyrins Phthalocyanines 2001; 5: 758-761).*
DE10146970_Machine Translation (2003).*

* cited by examiner

*Primary Examiner* — Jake Vu
(74) *Attorney, Agent, or Firm* — BJ Associates; Bolesh J Skutnik

(57) ABSTRACT

Biologically active compounds are provided that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, ophthalmological or urological disorders as well as providing methods to obtain them in pharmaceutical quality. One embodiment consists of a method to synthesize a porphyrin with a defined arrangement of meso-substituents and then converting this porphyrin system to a chlorin system by dihydroxylation or reduction, and if more than one isomer is formed separate them by chromatography either on normal or reversed phase silica. In another embodiment the substituents on the porphyrin are selected to direct the reduction or dihydroxylation to the chlorin so that a certain isomer is selectively formed. Another embodiment is to provide amphiphilic compounds with a higher membrane affinity and increased PDT-efficacy. In another embodiment a method to reductively cleave the osmate(VI)ester avoiding the use of gaseous $H_2S$ is provided. In another embodiment substituents are identified that via their steric and/or electronic influence direct the dihydroxylation or reduction with diimine so that one isomer is favored. Another embodiment consists of formulate the desired isomer into a liposomal formulation to be injected avoiding undesirable effects like solubility problems or delayed pharmacokinetics of the tetrapyrrole systems.

18 Claims, 9 Drawing Sheets

$R^1$ = nonpolar substituent
$R^2$ = polar substituent
$R^3$ = H or OH, M = 2 H or metal.

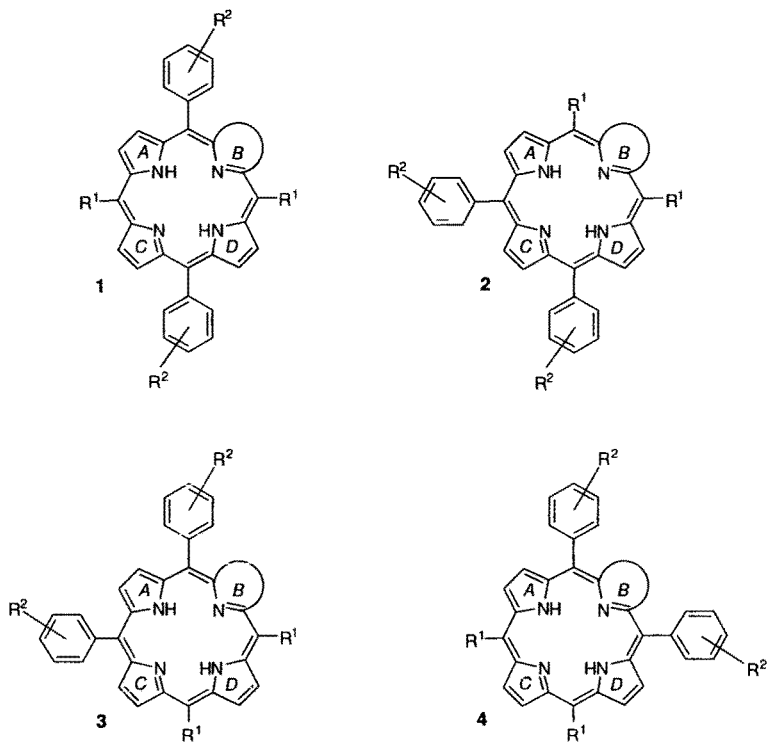

Wherein:

B is:

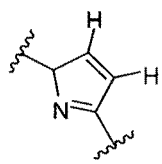 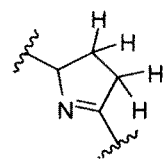 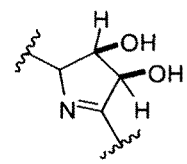 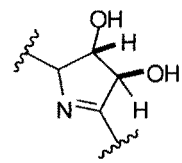

porphyrin system     chlorin system     chlorin system     chlorin system $R^1$ is:    a substituted or unsubstituted alkyl group consisting of 4-15 carbon atoms $R^2$ is    a substituent either in the *meta-* or *para-* position of the phenyl ring with $R^2$ = -OH, -COOH, -NH$_2$, -COOX, -NHX, OX, -NH-Y-COOH, or -CO-Y-NH$_2$.

Wherein:

X is    a polyethyleneglycol-residue with (CH$_2$CH$_2$O)$_n$CH$_3$ with n = 1–30 or a carbohydrate moiety Y is    peptides or oligopeptides wherein n=1–30.

Figure 2

METHOD AND APPLICATION OF UNSYMMETRICALLY *MESO*-SUBSTITUTED PORPHYRINS AND CHLORINS FOR PDT

NATIONAL FILING UNDER 35 USC 371

This application is being filed as a US National stage under 35 USC 371 of PCT Application No. PCT/US09/57283, which was filed Sep. 17, 2009 and also claims the benefit of U.S. Provisional Application Ser. No. 61/098,026 filed Sep. 18, 2008, both of which are incorporated by reference herein.

BACKGROUND OF THE INVENTION

1. Field of the Invention

The invention relates to the chemistry of biologically active compounds. More particularly to specifically substituted porphyrin and chlorin derivatives that can be used as photosensitizers for a wide range of light irradiation treatments such as photodynamic therapy of cancer, infections and other diseases.

2. Invention Disclosure Statement

Photodynamic therapy (PDT) is one of the most promising new techniques now being explored for use in a variety of medical applications (Photodynamic therapy, basic principles and clinical applications. Eds. B. W. Henderson, Th. J. Dougherty, Marcel Dekker, 1992, New York), and particularly is a well-recognized treatment for the destruction of tumors (Photodynamic tumor therapy. $2^{nd}$ and $3^{rd}$ generation photosensitizers. Ed. J. G. Moser, Harwood Academic Publishers, 1998, Amsterdam). Photodynamic therapy uses light and a photosensitizer (a dye) to achieve its desired medical effect. A large number of naturally occurring and synthetic dyes have been evaluated as potential photosensitizers for photodynamic therapy. Perhaps the most widely studied class of photosensitizers are the tetrapyrrolic macrocyclic compounds. Among them, especially porphyrins and chlorins have been tested for their PDT efficacy. Porphyrins are macrocyclic compounds with bridges of one carbon atom joining pyrroles to form a characteristic tetrapyrrole ring structure. There are many different classes of porphyrin derivatives including those containing dihydro-pyrrole units. Chlorins, as referred to in the present invention, are porphyrin derivatives containing one dihydro-unit whereas bacteriochlorins are characterized by two dihydro-pyrrole units (in general in chlorins one double bond of the aromatic system in β-position is absent and in bacteriochlorins two opposite double bonds are absent compared to the porphyrin). As examples of tetrapyrrolic macrocyclic compounds used as photosensitizers, U.S. Pat. No. 4,656,186 from Bommer et. al. discloses fluorescent mono, di- or polyamide of an aminocarboxilic acid and tetrapyrrole containing at least three carboxy groups, U.S. Pat. No. 7,022,843B1 from MacAlpine et. al. provides β,β'-dihydroxy meso-substituted chlorin as photosensitizers, and U.S. Pat. No. 7,166,719B2 from Pandey et. al. discloses tetrapyrrole compounds containing a fluorinated substituent where the compound is a chlorin or a bacteriochlorin for PDT diagnostic and therapeutic application.

There are several properties that an effective photosensitizer should accomplish. Among them, a desirable characteristic in order to efficiently destroy deep target tissues is a strong absorption at long wavelength. Many current photosensitizers are not efficient enough as they have low absorption in the red region of the spectrum. Chlorins have the advantage that they possess an intense absorption in the red and near-infrared region of the electromagnetic spectrum. As light of longer wavelength penetrates deeper into the tissue, it is thus possible to treat e.g. more expanded tumors, if the PDT is employed for tumor therapy. Chlorins possessing potential for PDT can either be derived from natural sources or from total synthesis.

If the chlorins are derived from natural compounds they are usually obtained by derivatizing chlorophylls or bacteriochlorophylls, as for example the photosensitizers derived from chlorophyll a of photosynthetic plants and algae disclosed in U.S. Pat. No. 5,330,741. Due to the sensibility of the natural compounds this is often difficult and requires vast resources. So, the synthesis of chlorins by total synthesis is an appealing alternative. Methods to prepare chlorins and bacteriochlorins by total synthesis are known in the art. Generally these compounds are prepared by first synthesizing the porphyrin and then converting the porphyrin system to a chlorin or bacteriochlorin system. This step can e.g. be performed by the reduction with in situ generated di-imine or by cis-dihydroxylation with osmium tetroxide; multistep reactions leading to trans-dihydroxylation are also known (patent EP 00337601B1; patent application WO 09613504A1, patent application WO 00061584A1; C. Brückner, D. Dolphin, 2,3-vic-Dihydroxy-meso-tetraphenylchlorins from the Osmium Tetroxide Oxidation of meso-Tetraphenylporphyrin, *Tetrahedron Lett.* 1995, 36, 3295-3298; C. Brückner, D. Dolphin, β,β'-Dihydroxylation of meso-Tetraphenylchlorins, *Tetrahedron Lett.* 1995, 36, 9425-9428; H. W. Daniell, S. C. Williams, H. A. Jenkins, C. Brückner, Oxidation of meso-tetraphenyl-2,3-dihydroxychlorin: simplified synthesis of β,β'-dioxochlorins, *Tetrahedron Lett.* 2003, 44, 4045-4049; F. Rancan, A. Wiehe, M. Nöbel, M. O. Senge, S. Al Omari, F. Böhm, M. John, B. Röder, influence of substitutions on asymmetric dihydroxychlorins with regard to intracellular uptake, sub cellular localization and photosensitization in Jurkat cells, *J. Photochem. Photobiol. B: Biology* 2005, 78, 17-28; I. Laville, T. Figueiredo, B. Loock, S. Pigaglio, Ph. Maillard, D. S. Grierson, D. Carrez, A. Croisy, J. Blais, Synthesis, Cellular Internalization and Photodynamic Activity of Glucoconjugated Derivatives of Tri and Tetra(meta-hydroxyphenyl)chlorines, *Bioorg. Med. Chem.* 2003, 11, 1643-1652). Mostly, compounds with four identical substituents in the meso-positions have been investigated and tested for their PDT efficacy. One prominent example is Temoporfin which is the active compound in the medicinal product Foscan® which is successfully used in Europe as a medicinal product for the PDT treatment of head and neck cancer. Also, all examples in the abovementioned patent application WO 09613504A1 are compounds with four identical meso substituents. The few publications on unsymmetrically tetrakis-meso-substituted chlorins derived from total synthesis that exist are of the so-called $A_3B$-type, i.e. incorporating 3 identical and one different meso-substituent (I. Laville, T. Figueiredo, B. Loock, S. Pigaglio, Ph. Maillard, D. S. Grierson, D. Carrez, A. Croisy, J. Blais, Synthesis, Cellular Internalization and Photodynamic Activity of Glucoconjugated Derivatives of Tri and Tetra(meta-hydroxyphenyl)chlorines, *Bioorg. Med. Chem.* 2003, 11, 1643-1652, F. Rancan, A. Wiehe, M. Nöbel, M. O. Senge, S. Al Omani, F. Böhm, M. John, B. Röder, Influence of substitutions on asymmetric dihydroxychlorins with regard to intracellular uptake, sub cellular localization and photosensitization in Jurkat cells. *J. Photochem. Photobiol. B: Biology* 2005, 78, 17-28; J. K. Macalpine, R. Boch, D. Dolphin, Evaluation of tetraphenyl-2,3-dihydroxychlorins as potential photosensitizers, *J. Porphyrins Phthalocyanines* 2002, 6, 146-155). One reason for using symmetrically substituted porphyrins to convert them into chlorins is that in this case no isomers are formed. If no isomers are formed the resulting compounds are easily characterized and prepared, a key factor for commercial production. If unsymmetrically substituted porphyrins are used to convert them into chlorins different regioisomers are formed which require subsequent separation (not in the case of a trans-arrangement of the substituents, cf. FIG. 2). Therefore, the chlorins with a meso-$A_3B$-substitution found in the art are often poorly characterized or are used as an isomeric mixture without separation (e.g. J. K. Macalpine, R. Bach, D. Dolphin, Evaluation of tetraphenyl-2,3-dihydroxychlorins as potential photosensitizers, *J. Porphyrins Phthalocyanines* 2002, 6, 146-155; I. Laville, T. Figueiredo, B. Loock, S. Pigaglio, Ph. Maillard, D. S. Grierson, D. Carrez, A. Croisy, J. Blais, Synthesis, Cellular Internalization and Photodynamic Activity of Glucoconjugated Derivatives of Tri and Tetra(meta-hydroxyphenyl)chlorines, *Bioorg. Med. Chem.* 2003, 11, 1643-1652). As it is difficult to purify the mixture in order to eliminate the isomers that do not contribute to the PDT effect or enrich the preparation with active compounds, it would be an advantage to find alternative unsymmetrically tetrakis-meso-substituted chlorins easily characterized and produced with simple preparation methods. Especially to seize the particular properties of unsymmetrically substituted chlorins, as they might increase the amphiphilicity of the compounds and thus their membrane affinity and PDT efficacy.

Thus, there is a need to enhance the effectiveness of prior art biologically active compounds used as photosensitizers in order to successfully perform a wide range of light irradiation treatments such as photodynamic therapy of cancer, infections and other diseases. Moreover, it is necessary to provide novel methods of preparation and application of unsymmetrically tetrakis-meso-substituted chlorins in order to provide enhanced photosensitizers than those available up to date. Thus, PDT efficacy would be increased by taking advantage of unsymmetrically tetrakis-meso-substituted chlorins properties, such as strong absorption at long wavelength of the red and near-infrared region of the electromagnetic spectrum for deeper tissue penetration, enhanced selectivity for tumors or other target tissues over healthy surrounding tissues due to its tailored amphiphilicity that increases membrane affinity, and custom-made pharmacokinetic behavior depending on the particular PDT application.

OBJECTIVES AND BRIEF SUMMARY OF THE INVENTION

It is an objective of the present invention to provide biologically active compounds that can be used as photosensitizers for a wide range of applications including light irradiation treatments such as photodynamic therapy of cancer, infections and other diseases.

It is a further objective of the present invention to use the chemically stable porphyrin and chlorin derivatives for various medical applications such as photodynamic therapy.

It is another objective of the present invention to provide unsymmetrically tetrakis-meso-substituted chlorin structures that can be used in the photodynamic therapy of tumors and other hyperproliferative diseases, dermatological disorders, viral or bacterial infections, ophthalmological disorders or urological disorders.

It is yet another object of the present invention to provide unsymmetrically tetrakis-meso-substituted chlorin structures that can be used for the fluorescence diagnosis and PDT treatment of a non-tumorous indication such as arthritis and similar inflammatory diseases.

It is still another object of the present invention to provide a method to prepare and purify such unsymmetrically tetrakis-meso-substituted chlorins and to provide a method for the separation of the isomers formed.

It is still a further object of the present invention to provide highly amphiphilic compounds to be used in the PDT-treatment of tumors, dermatological disorders, viral or bacterial infections, ophthalmological disorders or urological disorders.

It is another object of the present invention to provide a method of preparation that can direct the dihydroxylation or reduction of the starting material so that the formation of one isomer is favored.

It is still another objective to provide pharmaceutically acceptable formulations for the biologically active compounds of the present invention such as liposomal formulation to be injected avoiding undesirable effects like precipitation at the injection site or delayed pharmacokinetics of the tetrapyrrole systems.

Briefly stated, the present invention provides Biologically active compounds that can be used as photosensitizers for diagnostic and therapeutic applications, particularly for PDT of cancer, infections and other hyperproliferative diseases, fluorescence diagnosis and PDT treatment of a non-tumorous indication such as arthritis, inflammatory diseases, viral or bacterial infections, dermatological, ophthalmological or urological disorders as well as providing methods to obtain them in pharmaceutical quality. One embodiment consists of a method to synthesize a porphyrin with a defined arrangement of meso-substituents and then converting this porphyrin system to a chlorin system by dihydroxylation or reduction, and if more than one isomer is formed separate them by chromatography either on normal or reversed phase silica. In another embodiment the substituents on the porphyrin are selected to direct the reduction or dihydroxylation to the chlorin so that a certain isomer is selectively formed. Another embodiment is to provide amphiphilic compounds with a higher membrane affinity and increased PDT-efficacy. In another embodiment a method to reductively cleave the osmate(VI)ester avoiding the use of gaseous $H_2S$ is provided. In another embodiment substituents are identified that via their steric and/or electronic influence direct the dihydroxylation or reduction with diimine so that one isomer is favored. Another embodiment consists of formulate the desired isomer into a liposomal formulation to be injected avoiding undesirable effects like solubility problems at injection or delayed pharmacokinetics of the tetrapyrrole systems The above and other objects, features and advantages of the present invention will become apparent from the following description read in conjunction with the accompanying drawings.

BRIEF DESCRIPTION OF FIGURES

FIG. 2 depicts an embodiment of the present invention showing the specifically substituted porphyrin derivatives, particularly the chlorin derivatives of types 1, 2, 3 or 4.

DETAILED DESCRIPTION OF PREFERRED EMBODIMENTS

The present invention provides biologically active compounds that can be used as photosensitizers for a wide range of light irradiation treatments such as photodynamic therapy of cancer, hyperproliferative diseases, dermatological disorders, viral or bacterial infectious diseases, opthalmological disorders and/or urological disorders. The alternative photosensitizers provided by the present invention have the advantage that they are easily produced and characterized. Moreover, as the present invention provides methods to tailor amphiphilic compounds for desired PDT applications, target tissue selectivity is increased and thus PDT efficacy. The present invention enhances the effectiveness of prior art biologically active compounds offering a deeper tissue penetration due to their strong absorption at long wavelength of the red and near-infrared region of the electromagnetic spectrum, enhanced selectivity for target tissues over healthy surrounding tissues due to its tailored amphiphilicity and custom-made pharmacokinetic behavior depending on the particular PDT application.

Figure 1:
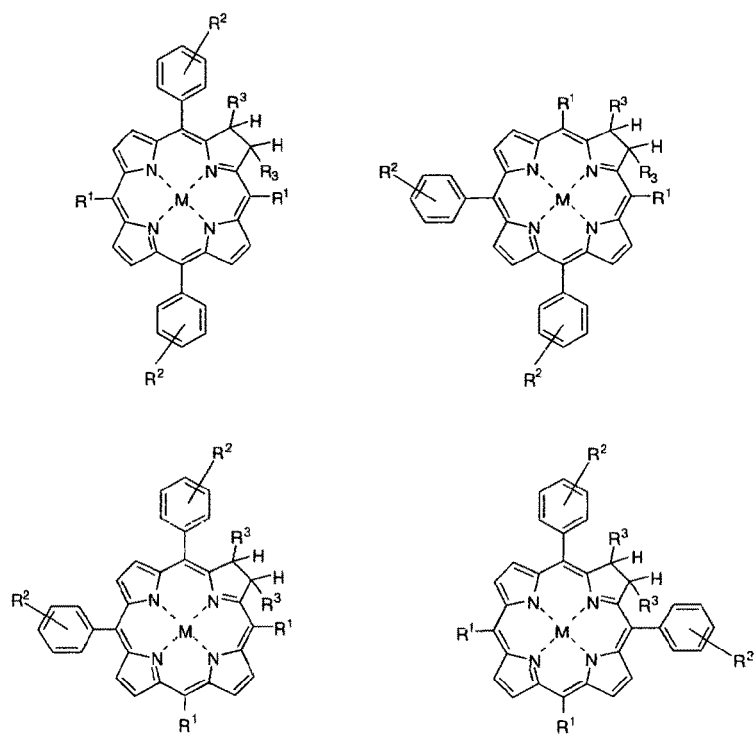
FIG. 1 shows examples of unsymmetrically tetrakis-meso-substituted chlorin structures combining two nonpolar (alkyl) and two polar meso-substituents that are specially suited for medical applications.

The biologically active compounds of the present invention that can be used for different medical indications, particularly PDT, are unsymmetrically tetrakis-meso-substituted chlorin structures. Indeed, it has been unexpectedly been found that chlorins combining two nonpolar (alkyl) and two polar meso-substituents in their structure, as illustrated in FIG. 1, are especially suited for such a medical application. Additionally, the novel invention extends its applications as it can be used for fluorescence diagnosis and PDT treatment of a non-tumorous indication such as arthritis and similar inflammatory diseases.

In order to obtain the novel photosensitizers the present invention uses the chemically stable porphyrin and chlorin derivatives according to formulae 1, 2, 3, and 4 shown in FIG. 2 and provides methods of preparation and separation of the isomers formed to obtain meso-alkyl substituted chlorins, more particularly the unsymmetrically tetrakis-meso-substituted chlorin structures that can be used in the photodynamic therapy. With respect to partially meso-alkyl substituted chlorins there is in fact only one example in the literature (F. Rancan, A. Wiehe, M. Nöbel, M. O. Senge, S. Al Omani. F. Böhm, M. John, B. Röder, Influence of substitutions on asymmetric dihydroxychlorins with regard to intracellular uptake, sub cellular localization and photosensitization in Jurkat cells, *J. Photochem. Photobiol. B: Biology* 2005, 78, 17-28; the compound is also of the meso-$A_3B$-substitution pattern). On the other hand, especially such unsymmetrically substituted chlorins, which are regio-isomerically pure (though in most cases there are still enantiomeric mixtures), could be of great interest as photosensitizers for PDT as such unsymmetric substitution might increase the amphiphilicity of the compounds and thus their membrane affinity and PDT efficacy. In addition, it has surprisingly been found during the investigations related to the present invention, that there are sometimes pronounced differences in PDT-efficacy between different chlorin isomers.

Figure 3:
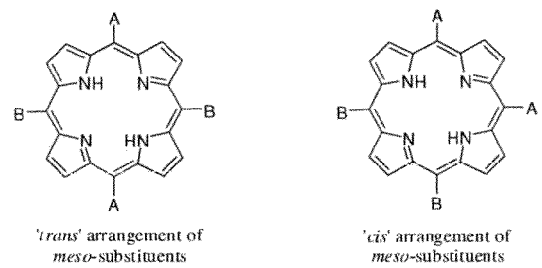
FIG. 3 shows an embodiment of the present invention depicting the arrangement of a porphyrin system to be converted to a chlorin system, where the porphyrin system is of the $A_2B_2$ type either with a "cis" or a "trans" arrangement of the meso-substituents and A is the nonpolar (alkyl) and B the polar substituent.

An embodiment of the present invention consists of a method to synthesize a porphyrin with a defined arrangement of meso-substituents [a porphyrin of the $A_2B_2$ type, either with a 'cis' or a 'trans' arrangement of the meso-substituents, as illustrated in FIG. 3, where e.g. A is the nonpolar (alkyl) and B the polar substituent] and then converting this porphyrin system to a chlorin system by dihydroxylation or reduction (as e.g. described in: M. Schroeder, Osmium Tetraoxide Cis Dihydroxylation of Unsaturated Substrates, *Chem. Rev.* 1980, 80, 187-213; R. Bonnett, R. D. White, U.-J. Winfield, M. C. Berenbaum, Hydroporphyrins of the meso-tetra(hydroxyphenyl)porphyrin series as tumor photosensitizers, *Biochem. J.* 1989, 261, 277-280). In a last step the isomers (if more than one isomer is formed) are separated by chromatography either on normal or reversed phase silica.

Another embodiment of the present invention consists of the steps of synthesizing a porphyrin with a defined arrangement of substituents, converting it to the chlorin, separating the isomers as described above and then to formulate the desired isomer into a liposomal formulation.

In yet another embodiment of the present invention a porphyrin of the 'trans'-$A_2B_2$-type is synthesized, converted to the dihydroxychlorin and purified by chromatography.

In yet another embodiment of the present invention, a porphyrin of the 'cis'-$A_2B_2$-type is synthesized, converted to the dihydroxychlorin and then the isomers are separated and purified by chromatography.

It has also been found that the substituents on the porphyrin due to their electronic and steric influence can direct the dihydroxylation, thus favoring the formation of one isomer. So, in yet another embodiment of the present invention the substituents on the porphyrin are selected to direct the reduction or dihydroxylation to the chlorin (examples 3.2 and 3.4) so that a certain isomer is selectively formed.

In a specifically preferred embodiment of the present invention a porphyrin of the 'trans'-$A_2B_2$-type is synthesized, having hexyl chains as substituent A and methoxycarbonyl phenyl residues as substituent B. Then this porphyrin is converted to the dihydroxychlorin and the remaining methylester is hydrolyzed to receive the corresponding carboxylic acid.

Acceptable starting materials for the synthesis of the chlorins which are the subject of the present invention are pyrrole and aldehydes. More specifically, pyrrole and two aldehydes, one alkanal and one aromatic aldehyde are employed for the synthesis of the unsymmetrically substituted porphyrins which are the basis of the synthesis of the corresponding chlorins. Pyrrole and aldehydes are subjected to a condensation reaction. Suitable methods for this condensation have long been known in the art (J. S. Lindsey, I. C. Schreiman, H. C. Hsu, P. C. Kearney and A. M. Marguerettaz, *J. Org. Chem.* 1987, 52, 827-836). Alternatively, the unsymmetrically substituted porphyrins can also be synthesized using di- or tripyrromethanes and aldehydes, as is also known in the art (C.-H. Lee, J. S. Lindsey, One-Flask Synthesis of Meso-Substituted Dipyrromethanes and Their Application in the Synthesis of Trans-Substituted Porphyrin Building Blocks, *Tetrahedron* 1994, 50, 11427-11440). After condensation and purification of the desired unsymmetrically substituted porphyrins these are converted to the chlorins. As there is only one example of a tetra-meso-substituted chlorin bearing only one alkyl-substituent known in the art, another embodiment of the present invention provides a method for the preparation of multiply meso-alkyl-substituted chlorins via dihydroxylation. The synthesis of meso-substituted chlorins bearing alkyl chains is exemplified with examples 3.1-3.4. Furthermore, the use of lipophilic alkyl-substituted porphyrins as substrates for the dihydroxylation is a key feature of the present invention as it gives access to amphiphilic compounds with a higher membrane affinity and increased PDT-efficacy. In examples 1.1 and 1.2 a series of unsymmetrically substituted porphyrins is synthesized with the objective to obtain porphyrins bearing both hydrophilic and hydrophobic groups.

The dihydroxylation of porphyrins with osmium tetroxide that is known in the art (cf. above Brückner, et al.) uses gaseous $H_2S$ to reductively cleave the osmate(VI)ester. The use of gaseous and toxic $H_2S$ is not favorable for the synthesis of compounds to be used eventually in large scale pharmaceutical preparations. Moreover, the use of hydrogen sulfide leads to impurities, making the chromatographic workup and the separation of the chlorin isomers difficult. Thus, another embodiment of the present invention provides a simple method for the reductive cleavage of the osmate(VI)ester that avoids the use of gaseous $H_2S$. Instead, a small amount of a saturated sodium bisulfite solution in water/methanol is used which is added to the reaction mixture. After stirring the mixture overnight the cleavage of the osmate ester to the diol proceeds quantitatively (examples 3.1-3.4). The resulting chlorin mixtures can easily be separated and purified by chromatography.

As the attack of osmium tetroxide or of the diimine can take place on any of the pyrrolic subunits, the reaction of the unsymmetrically substituted porphyrins in the case of the 'cis'-$A_2B_2$-type porphyrins leads to the formation of 3 regioisomers, whereas for the 'trans'-$A_2B_2$-type only one regioisomer is formed. Therefore, in another embodiment the present invention identifies substituents that via their steric and/or electronic influence direct the dihydroxylation or reduction with diimine so that one isomer is favored. In the course of the investigations related to the present invention it turned out that for 'cis'-$A_2B_2$-type porphyrins (with A=hexyl) the pyrrolic subunit between hexyl-groups (example 3.2 and 3.4) is preferred for dihydroxylation. This degree of selectivity may be caused by simple steric and/or electronic effects. The structure of the different regioisomers was unequivocally determined by 2D-NMR-spectroscopy (COSY, HMQC and HMBC). Already the $^1H$ NMR spectra show the influence of the dihydroxylated pyrrolic subunit on the nearby groups in the meso-positions. Interestingly, as the dipole moment of the chlorins is affected by the position of the diol also the chromatographic behavior of the compounds in most cases reflects the structure of the corresponding regioisomers.

The use of specifically substituted amphiphilic porphyrin and chlorin derivatives produced according to the present invention is suitable to be used for photodynamic therapy of cancer and other hyperproliferative diseases and infections. In another embodiment, aimed to obtain such amphiphilic compounds, the methyl ester groups of some porphyrins and dihydroxychlorins were hydrolyzed under basic conditions to provide the corresponding carboxylic acids (example 2 and 4). These acids have an increased solubility in polar solvents, increasing their potential as photosensitizers.

Figure 6A:
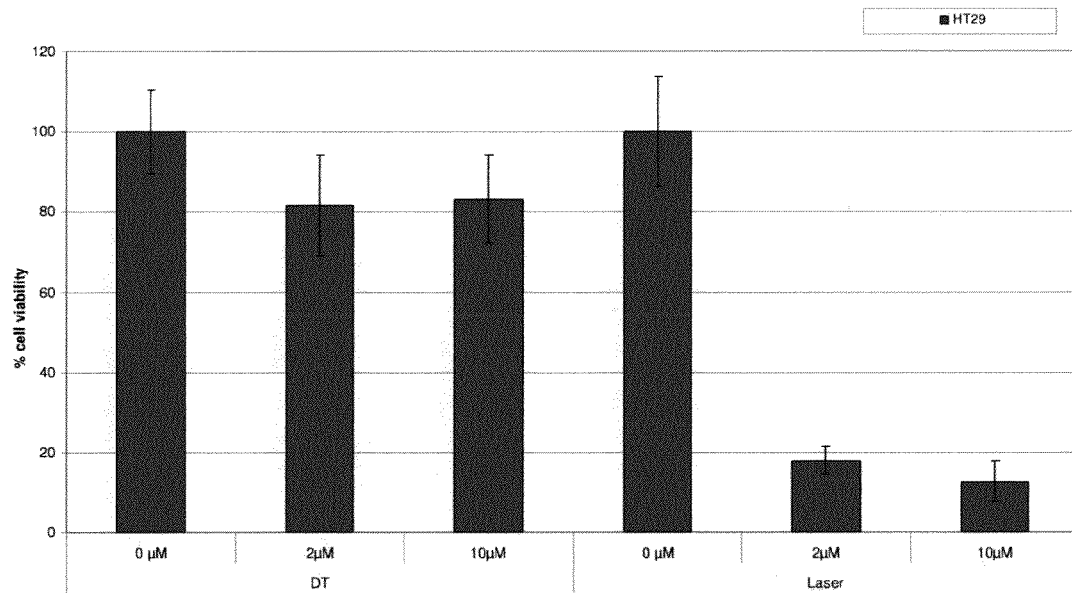
FIG. 6A illustrates the PDT activity of a liposomal formulation of 5,15-bis-(4-carboxyphenyl)-10,20-dihexyl-7,8-dihydroxy-7,8-chlorin in HT 29 cell line (DT: dark toxicity; Laser: photo toxicity).
Figure 6B:
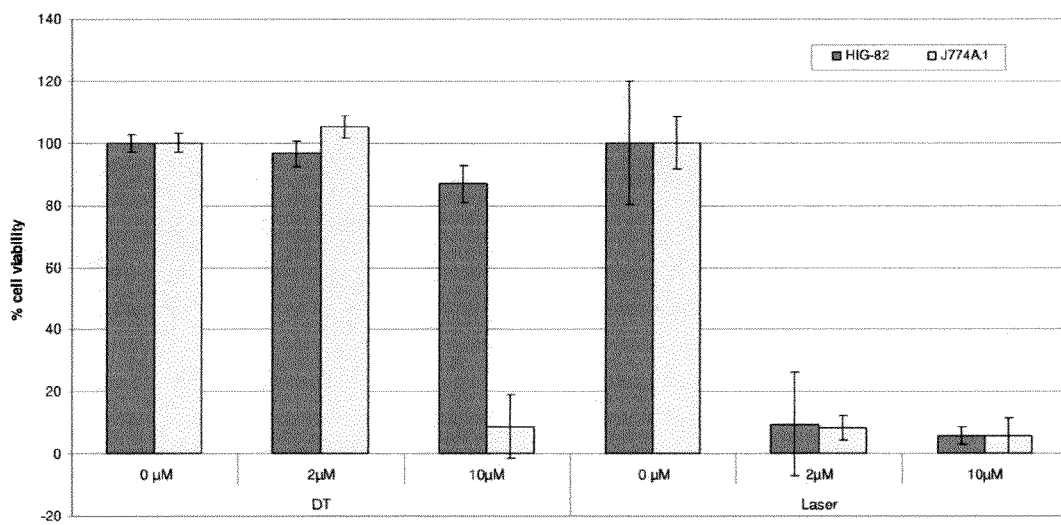
FIG. 6B illustrates the PDT activity of a liposomal formulation of 5,15-bis-(4-carboxyphenyl)-10,20-dihexyl-7,8-dihydroxy-7,8-chlorin in the HIG82 and J774A.1 cell lines (DT: dark toxicity; Laser: photo toxicity).

PDT is accomplished by first incorporating the derivatives into a pharmaceutically acceptable application vehicle (e.g. ethanolic solution or liposomal formulation) for delivery of the derivatives to a specific treatment site. After administering the derivatives in the vehicle to a treatment area, sufficient time is allowed so that the porphyrin and chlorine derivatives preferentially accumulate in the diseased tissue. Lastly, the treatment area is irradiated with light of a proper wavelength and sufficient power to activate the porphyrin derivatives to induce necrosis or apoptosis in the cells of said diseased tissue. Thus, one of the main advantages is that convenient pharmaceutical formulations can be created for the biologically active compounds of the present invention such as liposomal formulation to be injected avoiding undesirable effects like precipitation at the injection site or delayed pharmacokinetics of the tetrapyrrole systems. Due to their amphiphilic nature, the chemically stable porphyrin and chlorin derivatives of the present invention can be prepared in various pharmaceutically acceptable and active preparations for different administration methods, e.g. injections. In a specifically preferred embodiment such amphiphilic compounds are formulated into liposomes (FIGS. 6A and 6B). This liposomal formulation can then be injected avoiding undesirable effects such as precipitation at the injection site or delayed pharmacokinetics of the tetrapyrrole systems.

Determination of dark toxicity (DT) and photo toxicity (FIG. 4A) of one specific chlorin derivative of the present invention, 5,15-bis-(4-carboxyphenyl)-10,20-dihexyl-7,8-dihydroxy-7,8-chlorin prepared according to example 4.1, in cell culture experiments with a HT 29 cell line showed the excellent properties of the compounds for use in PDT. Further examples of the good phototoxic properties of the compounds of the present invention are illustrated with FIGS. 4B and 4C. The additional FIGS. 4D to 4F of experiments in the HT 29 cell line are included to illustrate that other dihydroxychlorins which do not possess a combination and arrangement of substituents as the one favored in the present invention show a less promising PDT activity.

As another object of the present invention is to use the disclosed porphyrin and chlorin derivatives in the diagnosis and treatment of arthritis and similar inflammatory diseases, the data presented in FIGS. 5A to 5D summarizes the results of the photodynamic treatment of two cell lines especially relevant for arthritis (HIG82 and J774A.1, a rabbit synoviocyte and a mouse macrophage cell line) with a series of compounds of the present invention. Again, a negative example (FIG. 5F) of a compound not having the favored combination of substituents and lacking the photodynamic activity is also included.

The following examples are presented to provide those of ordinary skill in the art with a full and illustrative disclosure and description of how to make the chlorin derivatives of the invention and show their photodynamic activity and are not intended to limit the scope of what the inventor regards as the invention. Efforts have been made to ensure accuracy with respect to numbers used (e.g. amounts, temperature etc.), but some experimental errors and deviations should be accounted for. Also, best measures have been taken to name the compounds with their systematic IUPAC name, nevertheless the basic reference are the given structural formulas based on the experimental spectroscopic data.

EXAMPLES

All reagents were used as purchased from commercial suppliers. Tetraacetyl-β-D-glucopyranosyloxy-benzaldehyde (I. Laville, S. Pigaglio, J.-C. Blais B. Loock, Ph. Maillard, D. S. Grieson, J. Blais, *Biorg. Med. Chem.* 2004, 12, 3673-3682) and 5-(4-methoxycarbonylphenyl)-dipyrromethane (B. J. Littler, M. A. Miller, C.-H. Hung, R. W. Wagner, D. F. O'Shea, P. D. Boyle, J. S. Lindsey, *J. Org. Chem.* 1999, 64, 1391-1396) were prepared according to the literature. Dichloromethane was purified by distillation over $K_2CO_3$ prior to use. Thin layer chromatography (TLC) was performed using Merck silica gel 60 (without fluorescence indicator) pre-coated on aluminium sheets. Flash chromatography was carried out using Merck silica gel 60, 0.040-0.063 mm (230-400 mesh). $^1H$ and $^{13}C$ NMR spectra were recorded in $CDCl_3$, $(CD_3)_2CO$ or $(CD_3)_2SO$ on Bruker AC 250, AC 500 or AMX 500 instruments. Chemical shifts δ are given in ppm relative to TMS as internal standard or relative to the resonance of the residual solvent peak, J values are given in Hz. Mass spectra were recorded on Varian MAT 771, Varian IonSpec QFT-7 or Agilent 6210 ESI-TOF instruments. Electronic absorption spectra were recorded on a Specord S300 (Analytik Jena) spectrophotometer using dichloromethane or acetone as solvent.

Example 1

Preparation of Unsymmetrical Substituted Porphyrins 1.1 Preparation of 5,15-dihexyl-10,20-bis-(4-methoxycarbonylphenyl)-porphyrin (method A) and 5,10-dihexyl-15,20-bis-(4-methoxycarbonylphenyl)-porphyrin In a typical experiment, dry dichloromethane (1500 ml) was placed in a three-necked flask equipped with a magnetic stirrer and argon gas inlet. After pyrrole (1.05 ml, 15 mmol), heptanal (1.05 ml, 7.5 mmol) and methyl 4-formylbenzoate (1.23 g, 7.5 mmol) were added, the flask was shielded from ambient light and TFA (1.16 ml, 15 mmol) was added and the reaction mixture was stirred at room temperature for 18 h. Then, DDQ (2.55 g, 11.25 mmol) suspended in dry dichloromethane (100 ml) was added. After further stirring for 1 h, triethylamine (3 ml) was added. To remove polymeric byproducts, the reaction mixture was filtered through silica gel. The solvent was evaporated and separation was achieved via flash chromatography with dichloromethane and further purification with dichloromethane/hexane 3:1 (first band) and dichloromethane (second and third band) as eluent. Further purification was achieved by recrystallization from dichloromethane/methanol The first band from the column contained 5,10,15-trihexyl-20-(4-methoxycarbonylphenyl)-porphyrin (203 mg, 12%), the second band the title compound 5,15-dihexyl-10,20-bis-(4-methoxycarbonylphenyl)-porphyrin (109 mg, 4%) and the third band the title compound 5,10-dihexyl-15,20-bis-(4-methoxycarbonylphenyl)-porphyrin (199 mg, 7%).

5,15-Dihexyl-10,20-bis-(4-methoxycarbonylphenyl)-porphyrin

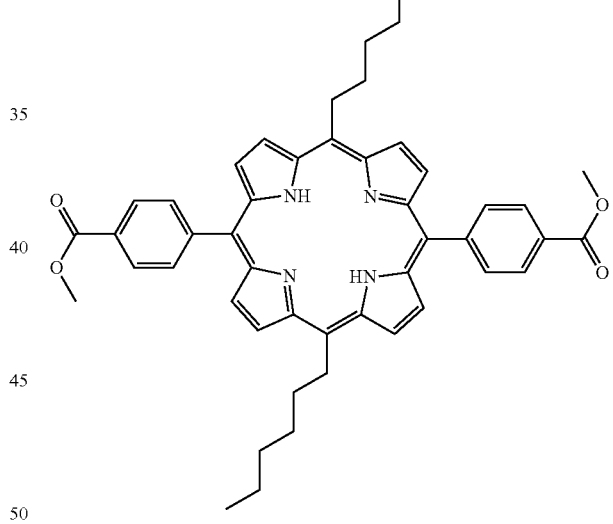

violet microcrystalline solid, mp 238° C.; $\lambda_{max}$ ($CH_2Cl_2$)/nm 421 (ε/dm³ mol⁻¹ cm⁻¹ 253500), 517 (13400), 553 (7600), 594 (3900) and 650 (5000); $\delta_H$ (250 MHz; $CDCl_3$) −2.71 (2H, s, NH), 0.92 (6H, t, J 7.3, 2×$CH_3$), 1.29-1.53 (8H, m, 4×$CH_2$), 1.76 (4H, $m_c$, 2×$CH_2$), 2.48 (4H, $m_c$, 2×$CH_2$), 4.14 (6H, s, 2×$OCH_3$), 4.89 (4H, t, J 7.7, 2×$CH_2$), 8.27 (4H, d, J 8.2, Ar), 8.45 (4H, d, J 8.2, Ar), 8.79 (4H, d, J 5.0, β-H), 9.40 (4H, d, J 5.0, β-H); $\delta_C$ (63 MHz; $CDCl_3$) 14.26 ($CH_3$), 22.84 ($CH_2$), 30.37 ($CH_2$), 32.04 ($CH_2$), 35.49 ($CH_2$), 38.89 ($CH_2$), 52.55 ($OCH_3$), 117.88 (meso-C), 120.48 (meso-C), 127.93 (Ar), 128.20 (Ar), 129.70 (Ar), 131.46 (Ar), 134.61 (Ar), 147.67 (Ar), 167.53 ($CO_2CH_3$); m/z (ESI) 747.3904 ([M+H]⁺, $C_{48}H_{51}N_4O_4^+$ requires 747.3905).

5,10-Dihexyl-15,20-bis-(4-methoxycarbonylphenyl)-porphyrin

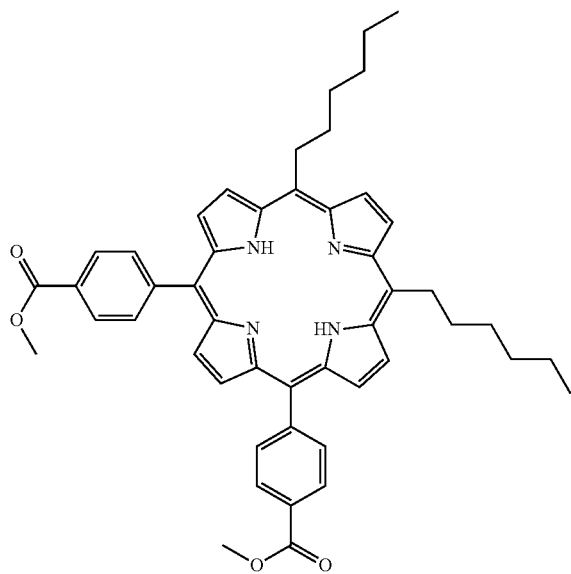 [SMILES: CCCCCCc1c2nc(c(CCCCCC)c3ccc([nH]3)c(-c3ccc(C(=O)OC)cc3)c3nc(c(-c4ccc(C(=O)OC)cc4)c4ccc1[nH]4)C=C3)C=C2]

violet microcrystalline solid, mp 131° C.; $\lambda_{max}$ ($CH_2Cl_2$)/nm 420 ($\epsilon$/dm$^3$ mol$^{-1}$ cm$^{-1}$ 263300), 519 (12000), 553 (7000), 596 (3900) and 652 (4000); $\delta_H$ (250 MHz; $CDCl_3$)-2.72 (2H, s, NH), 0.95 (6H, t, J 7.3, 2×$CH_3$), 1.45 (8H, m$_e$, 4×$CH_2$), 1.79 (4H, m$_c$, 2×$CH_2$), 2.52 (4H, m$_c$, 2×$CH_2$), 4.12 (6H, s, 2×$OCH_3$), 4.91 (4H, t, J 8.2, 2×$CH_2$), 8.24 (4H, d, J 8.2, Ar), 8.43 (4H, d, J 8.2, Ar), 8.69 (2H, s, β-H), 8.78 (2H, d, J 5.0, β-H), 9.41 (2H, d, J 5.0, β-H), 9.50 (2H, s, β-H); $\delta_C$ (63 MHz; $CDCl_3$) 14.30 ($CH_3$), 22.89 ($CH_2$), 30.43 ($CH_2$), 32.06 ($CH_2$), 35.86 ($CH_2$), 39.06 ($CH_2$), 52.53 ($OCH_3$), 117.49 (meso-C), 120.98 (meso-C), 128.05 (Ar), 128.63 (Ar), 129.68 (Ar), 130.88 (Ar), 134.63 (Ar), 147.30 (Ar), 167.51 ($CO_2CH_3$); m/z (ESI) 747.3932 ([M+H]$^+$, $C_{48}H_{51}N_4O_4^+$ requires 747.3905).

1.2 Preparation of 5,15-dihexyl-10,20-bis-(4-methoxycarbonylphenyl)-porphyrin (method B)

In a typical experiment, acetonitrile (500 ml) was placed in a three-necked flask equipped with a magnetic stirrer and argon gas inlet. After 5-(4-methoxycarbonylphenyl)-dipyrromethane (714 mg, 2.6 mmol) and heptanal (0.36 ml, 2.6 mmol) were added, the flask was shielded from ambient light and TFA (0.2 ml, 2.6 mmol) was added and the reaction mixture was stirred at room temperature for 18 h. Then, DDQ (860 mg, 3.8 mmol) suspended in acetonitrile (30 ml) was added. After further stirring for 1 h, triethylamine (1 ml) was added. The solvent was evaporated and preliminary purification was achieved via flash chromatography with dichloromethane/methanol 95:5 as eluent and further purification via flash chromatography with dichloromethane/ethylacetate 99:1 as eluent. The title compound 5,15-dihexyl-10,20-bis-(4-methoxycarbonylphenyl)-porphyrin was obtained after recrystallization from dichloromethane/methanol (81 mg, 9%).

1.3 Preparation of 5,15-bis-(3-hydroxyphenyl)-10,20-bis-(tridecyl)-porphyrin and 5,10-bis-(3-hydroxyphenyl)-15,20-bis-(tridecyl)-porphyrin In a typical experiment, dry dichloromethane (1500 ml) was placed in a three-necked flask equipped with a magnetic stirrer and argon gas inlet. After pyrrole (1.05 ml, 15 mmol), tetradecanal (1593 mg, 7.5 mmol) and 3-hydroxybenzaldehyde (916 mg, 7.5 mmol) were added, the flask was shielded from ambient light and TFA (1.16 ml, 15 mmol) was added and the reaction mixture was stirred at room temperature for 4 h. Then, DDQ (2.55 g, 11.25 mmol) suspended in dry dichloromethane (100 ml) was added. After further stirring for 1 h, triethylamine (6 ml) was added. To remove polymeric by-products, the reaction mixture was filtered through silica gel. The solvent was evaporated and separation was achieved via repeated flash chromatography with dichloromethane/ethylacetate 90:10 and 95:5 as eluent. Further purification was achieved by recrystallization from dichloromethane/aqueous methanol The first band from the column contained 5-(3-hydroxyphenyl)-10,15,20-tris-(tridecyl)-porphyrin (68 mg, 4%), the second band the title compound 5,15-bis-(3-hydroxyphenyl)-10,20-bis-(tridecyl)-porphyrin (52 mg, 2%) and the third band the title compound 5,10-bis-(3-hydroxyphenyl)-15,20-bis-(tridecyl)-porphyrin (114 mg, 4%).

5,15-Bis-(3-hydroxyphenyl)-10,20-bis-(tridecyl)-porphyrin

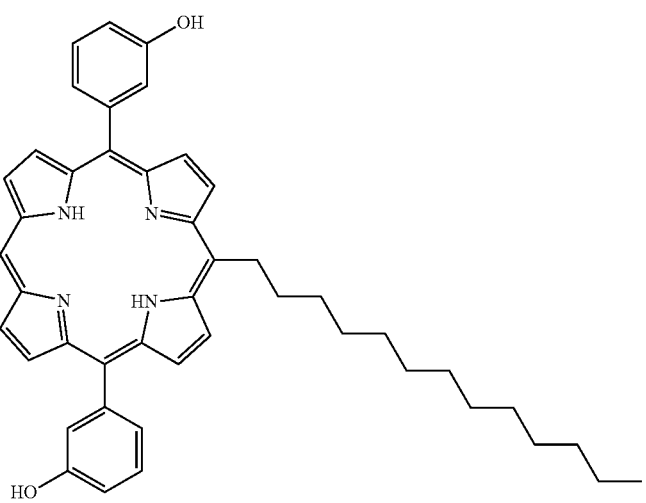

violet microcrystalline solid, mp 133° C.; $\delta_H$ (500 MHz; CDCl$_3$) −2.70 (2H, s, NH), 0.87 (6H, t, J 7.0, 2×CH$_3$), 1.25-1.33 (32H, m, 16×CH$_2$), 1.46 (4H, m$_c$, 2×CH$_2$), 1.72 (4H, m$_c$, 2×CH$_2$), 2.46 (4H, m$_c$, 2×CH$_2$), 4.84 (4H, t, J 8.0, 2×CH$_2$), 7.15-7.17 (2H, Ar), 7.46-7.47 (2H, m, Ar), 7.54 (2H, d, J 7.5, Ar), 7.73 (2H, d, J 7.5, Ar), 8.83 (4H, d, J 4.7, β-H), 9.33 (4H, d, J 4.7, β-H); $\delta_C$ (125 MHz; CDCl$_3$) 14.1 (CH$_3$), 22.7 (CH$_2$), 29.3 (CH$_2$), 29.6 (CH$_2$), 29.7 (CH$_2$), 30.5 (CH$_2$), 31.9 (CH$_2$), 35.2 (CH$_2$), 38.7 (CH$_2$), 114.6 (Ar), 118.2 (meso-C), 119.9 (meso-C), 121.7 (Ar), 127.5 (Ar), 127.6 (β-C), 131.6 (β-C), 144.1 (Ar), 153.7 (Ar); m/z (EI) 858 ([M]$^+$, 100%), 689 ([M-C$_{12}$H$_{15}$]$^+$, 87), 429 ([M]$^{2+}$, 9).

5,10-Bis-(3-hydroxyphenyl)-15,20-bis-(tridecyl)-porphyrin

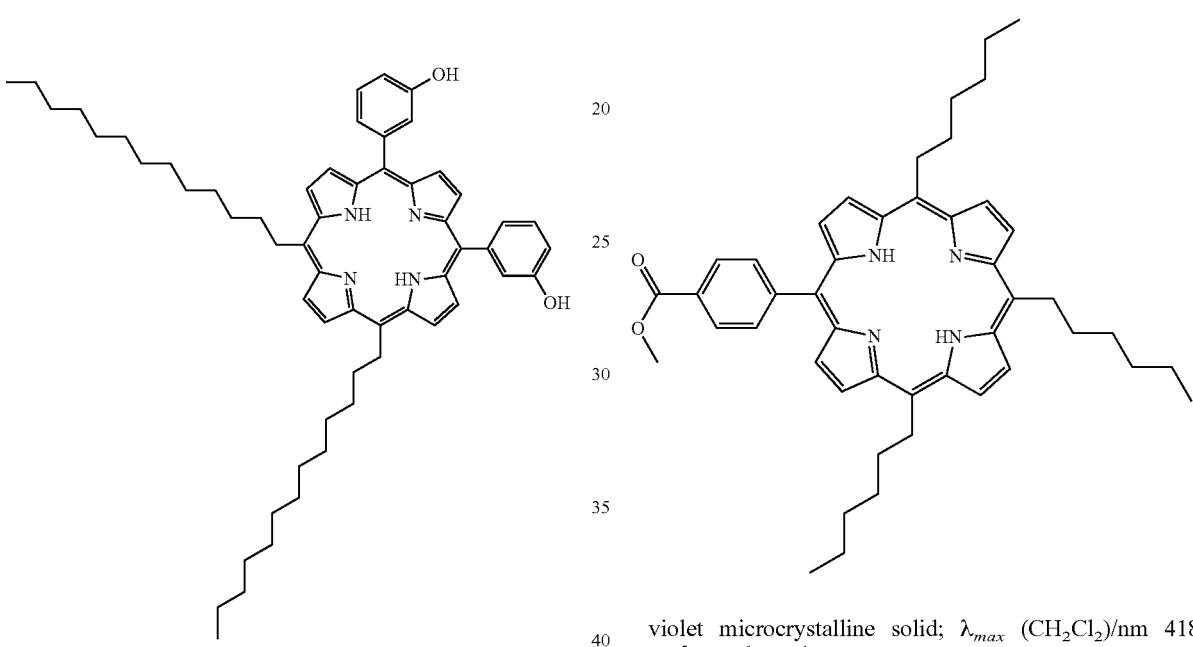

violet microcrystalline solid, mp 113° C.; $\delta_H$ (500 MHz; CDCl$_3$) −2.68 (2H, s, NH), 0.88 (6H, t, J 6.9, 2×CH$_3$), 1.27-1.37 (32H, m, 16×CH$_2$), 1.46-1.52 (4H, m, 2×CH$_2$), 1.72-1.78 (4H, m, 2×CH$_2$), 2.46-2.52 (4H, m, 2×CH$_2$), 4.86 (4H, t, J 7.0, 2×CH$_2$), 6.93-7.09 (2H, m, Ar), 7.25-7.30 (2H, m, Ar), 7.38-7.46 (2H, m, Ar), 7.56-7.65 (2H, m, Ar), 8.54-8.62 (2H, m, β-H), 8.75-8.79 (2H, m, β-H), 9.30 (2H, d, J 4.8, β-H) 9.49 (2H, s, β-H); $\delta_C$ (125 MHz; CDCl$_3$) 14.1 (CH$_3$), 22.7 (CH$_2$), 29.7 (CH$_2$), 30.6 (CH$_2$), 31.9 (CH$_2$), 35.6 (CH$_2$), 38.9 (CH$_2$), 114.5 (Ar), 118.0 (mesa-C), 120.3 (meso-C), 121.6 (Ar), 127.5 (Ar), 127.6 (Ar), 143.5 (Ar), 153.6 (Ar); m/z (EI) 858 ([M]$^+$, 100%), 689 ([M-C$_{12}$H$_{15}$]$^+$, 36), 520 ([M-2 C$_{12}$H$_{15}$]$^+$, 6), 429 ([M]$^{2+}$, 4).

1.3 Preparation of 5,10,15-trihexyl-20-(4-methoxy-carbonylphenyl)-porphyrin

In a typical experiment, dry dichloromethane (1500 ml) was placed in a three-necked flask equipped with a magnetic stirrer and argon gas inlet. After pyrrole (10.5 ml, 150 mmol), heptanal (15.8 ml, 113 mmol) and methyl 4-formylbenzoate (6.2 g, 38 mmol) were added, the flask was shielded from ambient light and TFA (2.15 ml, 28 mmol) was added and the reaction mixture was stirred at room temperature for 18 h. Then, DDQ (25 g, 110 mmol) suspended in dry dichloromethane (100 ml) was added. After further stirring for 1 h, triethylamine (6 ml) was added. To remove polymeric by-products, the reaction mixture was filtered through silica gel. The solvent was evaporated and separation was achieved via flash chromatography with dichloromethane and further purification with dichloromethane/hexane 3:1. Further purification was achieved by recrystallization from dichloromethane/methanol The first band from the column contained 5,10,15,20-tetrahexyl-porphyrin (930 mg, 5%), the second band the title compound 5,10,15-trihexyl-20-(4-methoxycarbonylphenyl)-porphyrin (1400 mg, 5%).

5,10,15-Trihexyl-20-(4-methoxycarbonylphenyl)-porphyrin violet microcrystalline solid; $\lambda_{max}$ (CH$_2$Cl$_2$)/nm 418 (ε/dm$^3$ mol$^{-1}$ cm$^{-1}$ 290300), 519 (14600), 553 (9100), 597 (4200) and 654 (6400); $\delta_H$ (250 MHz; CDCl$_3$) −2.68 (2H, s, NH), 0.92-1.06 (9H, m, 3×CH$_3$), 1.33-1.60 (12H, m, 6×CH$_2$), 1.73-1.88 (6H, m, 3×CH$_2$), 2.43-2.60 (6H, m, 3×CH$_2$), 4.14 (3H, s, OCH$_3$), 4.85-4.96 (6H, m, CH$_2$), 8.25 (2H, d, J 8.2, Ar), 8.43 (2H, d, J 8.2, Ar), 8.73 (2H, d, J 5.5, β-H), 9.36 (2H, d, J 5.5, β-H), 9.45 (2H, d, J 5.5, β-H), 9.48 (2H, d, J 5.5, β-H); $\delta_C$ (63 MHz; CDCl$_3$) 14.30 (CH$_3$), 22.89 (CH$_2$), 22.93 (CH$_2$), 30.39 (CH$_2$), 30.46 (CH$_2$), 32.07 (CH$_2$), 35.37 (CH$_2$), 35.96 (CH$_2$), 38.83 (CH$_2$), 39.04 (CH$_2$), 52.51 (OCH$_3$), 116.54 (meso-C), 119.51 (meso-C), 120.01 (meso-C), 127.95 (Ar), 128.26 (Ar), 129.52 (Ar), 130.84 (Ar), 134.63 (Ar), 147.77 (Ar), 167.58 (CO$_2$CH$_3$); m/z (PSI) 697.4467 ([M+H]$^+$ C$_{46}$H$_{57}$N$_4$O$_2$$^+$ requires 697.4476).

Example 2

Preparation of Unsymmetrical Carboxy-Substituted Porphyrins 2.1 Preparation of 5,15-bis-(4-carboxyphenyl)-10,20-dihexyl-porphyrin In a typical experiment, a solution of KOH (200 mg, 3.6 mmol) in methanol (1 ml) was added to a stirred solution of 5,15-dihexyl-10,20-bis-(4-methoxycarbonylphenyl)-porphyrin (31 mg, 0.04 mmol) in THF (8 ml) and the reaction mixture was stirred for 2 d. Water (50 ml) and hydrochloric acid were then added until the pH was adjusted to 4-6. The aqueous layer was extracted with dichloromethane (2×100 ml) and the organic layer was separated, washed with water until neutral and dried over sodium sulfate. The solvent was evaporated and the title compound 5,15-bis-(4-carboxyphenyl)-10,20-dihexyl-porphyrin was obtained after recrystallization from dichloromethane/aqueous methanol (26 mg, 87%).

5,15-Bis-(4-carboxyphenyl)-10,20-dihexyl-porphyrin

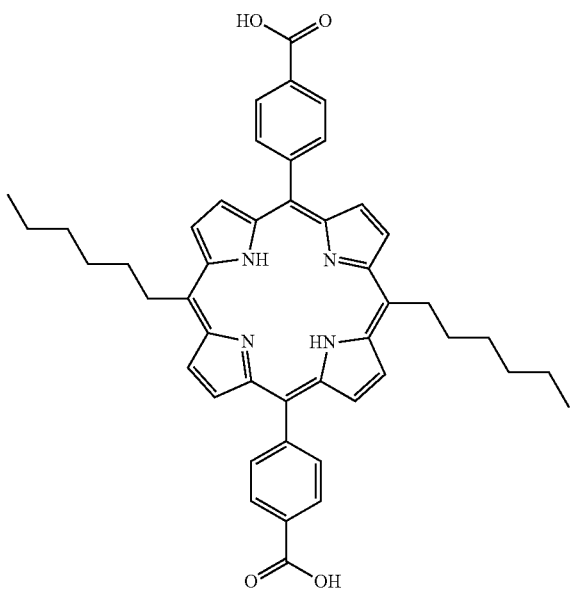 [SMILES: CCCCCCc1c2nc(c(-c3ccc(C(=O)O)cc3)c3ccc([nH]3)c(CCCCCC)c3nc(c(-c4ccc(C(=O)O)cc4)c4ccc1[nH]4)C=C3)C=C2]

violet microcrystalline solid, $\delta_H$ (250 MHz; $(CD_3)_2SO$) −2.96 (2H, s, NH), 0.81 (6H, t, J 7.1, 2×CH$_3$), 1.15-1.41 (8H, m, 4×CH$_2$), 1.60-1.71 (4H, m, 2×CH$_2$), 2.25-2.37 (4H, m, 2×CH$_2$), 4.81-4.86 (4H, m, 2×CH$_2$), 8.21 (4H, d, J 8.1, Ar), 8.33 (4H, d, J 8.1, Ar), 8.71 (4H, d, J 4.8, β-H), 9.57 (4H, d, J 4.8, β-H); m/z (ESI) 719.3621 ([M+H]$^+$, $C_{46}H_{47}N_4O_4^+$ requires 719.3592).

2.2 Preparation of 5,10-bis-(4-carboxyphenyl)-15,20-dihexyl-porphyrin

In a typical experiment, a solution of KOH (200 mg, 3.6 mmol) in methanol (1 ml) was added to a stirred solution of 5,10-dihexyl-15,20-bis-(4-methoxycarbonylphenyl)-porphyrin (34 mg, 0.05 mmol) in THF (8 ml) and the reaction mixture was stirred for 2 d. Water (50 ml) and hydrochloric acid were then added until the pH was adjusted to 4-6. The aqueous layer was extracted with dichloromethane (2×100 ml) and the organic layer was separated, washed with water until neutral and dried over sodium sulfate. The solvent was evaporated and the title compound 5,10-bis-(4-carboxyphenyl)-15,20-dihexyl-porphyrin was obtained after recrystallization from dichloromethane/aqueous methanol (26 mg, 79%).

5,10-bis-(4-carboxyphenyl)-15,20-dihexyl-porphyrin

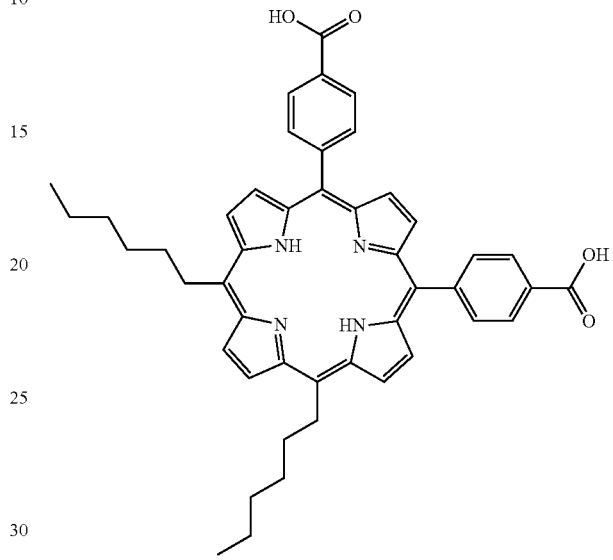

violet microcrystalline solid, $\delta_H$ (250 MHz; $(CD_3)_2SO$) −2.99 (2H, s, NH), 0.81 (6H, t, J 7.0, 2×CH$_3$), 1.19-1.41 (8H, m, 4×CH$_2$), 1.60-1.71 (4H, m, 2×CH$_2$), 2.25-2.36 (4H, m, 2×CH$_2$), 4.78-4.83 (4H, m, 2×CH$_2$), 8.18 (4H, d, J 8.0, Ar), 8.30 (4H, d, J 8.0, Ar), 8.63 (2H, s, β-H), 8.69 (2H, d, J 4.7, β-H), 9.54 (2H, d, J 4.7, β-H), 9.62 (2H, s, β-H); m/z (ESI) 719.3611 ([M+H]$^+$, $C_{46}H_{47}N_4O_4^+$ requires 719.3592).

Example 3

Preparation of Unsymmetrically Substituted cis-dihydroxychlorins 3.1 Preparation of 5,15-dihexyl-7,8-dihydroxy-10, 20-bis-(4-methoxy-carbonylphenyl)-7,8-chlorin In a typical experiment, a solution of osmium tetroxide (40 mg, 0.16 mmol) in dichloromethane/pyridine 30% (4 ml) was added to a stirred solution of 5,15-dihexyl-10,20-bis-(4-methoxycarbonylphenyl)-porphyrin (90 mg, 0.12 mmol) in dichloromethane/pyridine 30% (9 ml). After stirring for 3 h a saturated solution of sodium bisulfate in water/methanol 1:1 (15 ml) was added and the mixture was stirred for 18 h. The reaction mixture was filtered through Celite and dried over sodium sulfate. The solvent was evaporated and the residue was purified by flash chromatography with dichloromethane/ethylacetate 95:5 as eluent, followed by recrystallization from dichloromethane/methanol. The first band from the column contained starting material (20 mg, 22%) and the second band the title compound 5,15-dihexyl-7,8-dihydroxy-10,20-bis-(4-methoxycarbonylphenyl)-7,8-chlorin (52 mg, 55%).

5,15-Dihexyl-7,8-dihydroxy-10,20-bis-(4-methoxycarbonylphenyl)-7,8-chlorin

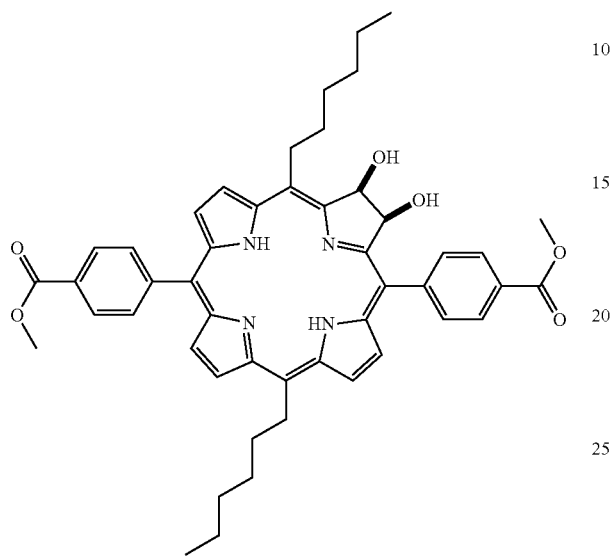

violet microcrystalline solid, mp 124° C.; $\lambda_{max}$ ($CH_2Cl_2$)/nm 411 ($\epsilon$/dm$^3$ mol$^{-1}$ cm$^{-1}$ 182900), 428 (159800), 524 (15500), 550 (18400), 594 (8200) and 646 (19200); $\delta_H$ (500 MHz; CDCl$_3$) −1.94 (2H, br s, NH), 0.89-0.95 (6H, m, 2×CH$_3$), 1.31-1.50 (8H, m, 4×CH$_2$), 1.67-1.76 (4H, m, 2×CH$_2$), 2.15-2.29 (2H, m, CH$_2$), 2.33-2.41 (2H, m, CH$_2$), 4.08 (3H, s, OCH$_3$), 4.11 (3H, s, OCH$_3$), 4.32-4.39 (1H, m, HCH), 4.48-4.54 (1H, m, HCH), 4.59-4.65 (2H, m, CH$_2$), 6.22 (1H, d, J 7.1, β-H), 6.45 (1H, d, J 7.1, β-H), 7.95 (1H, d, J 7.3, Ar), 8.04 (1H, d, J 7.4, Ar), 8.15 (2H, d, J 8.3, Ar), 8.19 (1H, d, J 5.0, β-H), 8.32-8.39 (4H, br m, Ar), 8.42 (1H, d, J 4.6, β-H), 8.61 (1H, d, J 4.9, β-H), 9.00 (1H, d, J 4.9, β-H), 9.06 (1H, d, J 4.6, β-H), 9.13 (1H, d, J 5.0, β-H); $\delta_C$ (125 MHz; CDCl$_3$) 14.26 (CH$_3$), 14.30 (CH$_3$), 22.81 (CH$_2$), 22.91 (CH$_2$), 30.33 (CH$_2$), 30.42 (CH$_2$), 31.98 (CH$_2$), 32.07 (CH$_2$), 33.38 (CH$_2$), 35.22 (CH$_2$), 36.76 (CH$_2$), 38.20 (CH$_2$), 52.55 (OCH$_3$), 73.60 (β-C), 74.05 (β-C), 111.35 (meso-C), 113.39 (meso-C), 120.54 (meso-C), 122.28 (β-C), 123.81 (meso-C), 124.14 (β-C), 124.86 (β-C), 127.97 (Ar), 128.62 (β-C), 128.73 (Ar), 129.32 (Ar), 129.65 (Ar), 129.75 (β-C), 129.81 (α-C), 132.35 (Ar), 133.09 (β-C), 134.03 (Ar), 134.27 (Ar), 135.72 (α-C), 139.04 (α-C), 141.43 (α-C), 146.84 (Ar), 147.29 (Ar), 151.59 (α-C), 153.67 (α-C), 159.05 (α-C), 162.79 (α-C), 167.26 (CO$_2$CH$_3$), 167.50 (CO$_2$CH$_3$); m/z (ESI) 781.3988 ([M+H]$^+$, C$_{48}$H$_{53}$N$_4$O$_6$$^+$ requires 781.3960).

3.2 Preparation of 5,10-dihexyl-7,8-dihydroxy-15,20-bis-(4-methoxy-carbonylphenyl)-7,8-chlorin, 5,20-dihexyl-7,8-dihydroxy-10,15-bis-(4-methoxycarbonylphenyl)-7,8-chlorin and 5,10-dihexyl-17,18-dihydroxy-15,20-bis-(4-methoxycarbonylphenyl)-17,18-chlorin In a typical experiment, a solution of osmium tetroxide (100 mg, 0.39 mmol) in dichloromethane/pyridine 30% (10 ml) was added to a stirred solution of 5,10-dihexyl-15,20-bis-(4-methoxycarbonylphenyl)-porphyrin (226 mg, 0.30 mmol) in dichloromethane/pyridine 30% (35 ml). After stirring for 20 h a saturated solution of sodium bisulfate in water/methanol 1:1 (40 ml) was added and the mixture was stirred for 18 h. The reaction mixture was filtered through Celite and dried over sodium sulfate. The solvent was evaporated and the residue was purified by flash chromatography with dichloromethane/ethylacetate 90:10 as eluent, followed by recrystallization from dichloromethane/methanol. The first band from the column contained starting material (38 mg, 18%), the second band the title compound 5,10-dihexyl-7,8-dihydroxy-15,20-bis-(4-methoxycarbonylphenyl)-7,8-chlorin (60 mg, 25%), the third band the title compound 5,20-dihexyl-7,8-dihydroxy-10,15-bis-(4-methoxycarbonylphenyl)-7,8-chlorin (74 mg, 31%) and the fourth band contained the title compound 5,10-dihexyl-17,18-dihydroxy-15,20-bis-(4-methoxycarbonylphenyl)-17,18-chlorin (22 mg, 9%).

5,10-Dihexyl-7,8-dihydroxy-15,20-bis-(4-methoxycarbonylphenyl)-7,8-chlorin

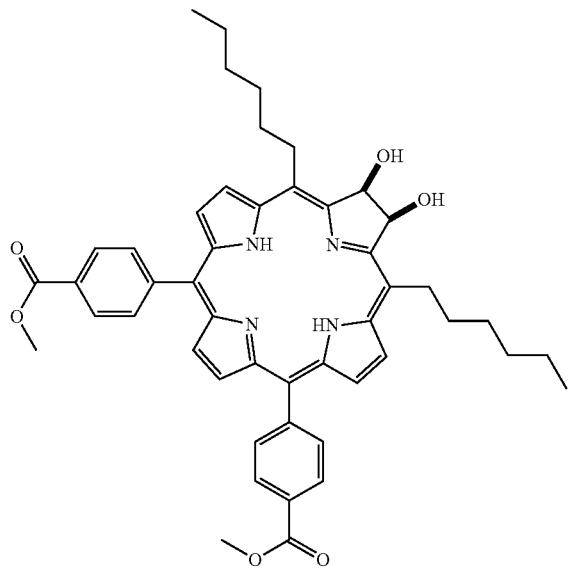 [SMILES: CCCCCCc1c2nc(c(CCCCCC)c3ccc([nH]3)c(-c3ccc(C(=O)OC)cc3)c3nc(c(-c4ccc(C(=O)OC)cc4)c4ccc1[nH]4)C=C3)[C@H](O)[C@@H]2O]

violet microcrystalline solid, mp 171-178° C.; $\lambda_{max}$ ($CH_2Cl_2$)/nm 410 ($\epsilon$/dm$^3$ mol$^{-1}$ cm$^{-1}$ 346000), 426 (339000), 526 (31100), 553 (38900), 596 (18100) and 648 (39400); $\delta_H$ (500 MHz; CDCl$_3$) −2.19 (2H, m, NH), 0.95 (6H, t, J 7.3 Hz, 2×CH$_3$), 1.36-1.49 (8H, m, 4×CH$_2$), 1.66-1.75 (4H, m, 2×CH$_2$), 2.09-2.23 (4H, m, 2×CH$_2$), 4.06 (6H, s, 2×OCH$_3$), 4.25-4.31 (2H, m, CH$_2$), 4.38-4.44 (2H, m, CH$_2$), 6.38 (2H, s, β-H), 7.90-7.98 (2H, br m, Ar), 8.02-8.09 (2H, br m, Ar), 8.14 (2H, br s, β-H), 8.28-8.30 (4H, m, Ar), 8.55 (2H, d, J 5.0, β-H), 8.95 (2H, d, J 5.0, β-H); $\delta_C$ (125 MHz; CDCl$_3$) 14.31 (CH$_3$), 22.93 (CH$_2$), 30.43 (CH$_2$), 32.04 (CH$_2$), 33.74 (CH$_2$), 36.86 (CH$_2$), 52.52 (OCH$_3$), 73.89 (β-C), 113.47 (meso-C), 120.15 (meso-C), 122.51 (β-C), 127.97 (β-C), 129.49 (β-C), 132.45 (Ar), 133.88 (Ar), 134.19 (Ar), 134.69 (α-C), 140.16

(α-C), 146.83 (Ar), 152.33 (α-C), 161.12 (α-C), 167.45 (CO$_2$CH$_3$); m/z (ESI) 781.3993 ([M+H]$^+$, C$_{48}$H$_{53}$N$_4$O$_6^+$ requires 781.3960).

5,20-Dihexyl-7,8-dihydroxy-10,15-bis-(4-methoxycarbonylphenyl)-7,8-chlorin

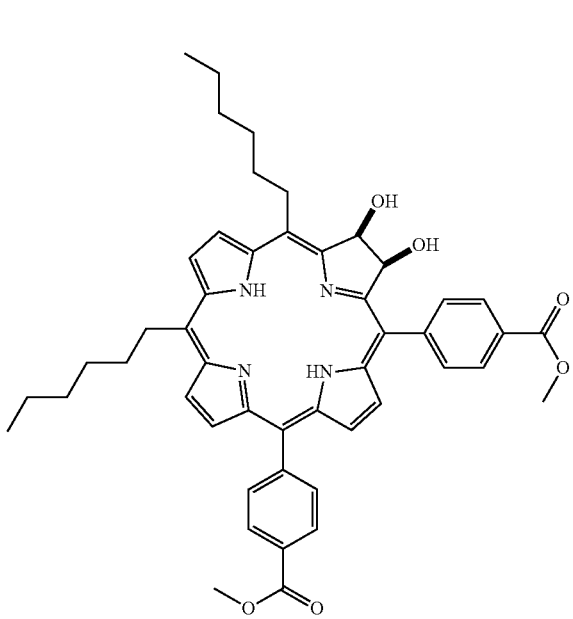 [SMILES: CCCCCCc1c2nc(c(-c3ccc(C(=O)OC)cc3)c3ccc([nH]3)c(-c3ccc(C(=O)OC)cc3)c3nc(c(CCCCCC)c4ccc1[nH]4)[C@@H](O)[C@H]3O)C=C2]

violet microcrystalline solid, mp 128° C.; λ$_{max}$ (CH$_2$Cl$_2$)/nm 409 (ε/dm$^3$ mol$^{-1}$ cm$^{-1}$ 175100), 428 (143800), 524 (14900), 551 (17800), 594 (8400) and 647 (19800); δ$_H$ (500 MHz; CDCl$_3$) −2.01 (1H, s, NH), −1.81 (1H, s, NH), 0.92-0.98 (6H, m, 2×CH$_3$), 1.34-1.52 (8H, m, 4×CH$_2$), 1.68-1.77 (4H, m, 2×CH$_2$), 2.12-2.20 (1H, m, HCH), 2.21-2.29 (1H, m, HCH), 2.34-2.40 (2H, m, CH$_2$), 4.05 (3H, s, OCH$_3$), 4.09 (3H, s, OCH$_3$), 4.29-4.35 (1H, m, HCH), 4.42-4.49 (1H, m, HCH), 4.53 (2H, t, 18.3 Hz, CH$_2$), 6.15 (1H, d, J 7.2, β-H), 6.37 (1H, d, J 7.2, β-H), 7.85 (1H, d, J 7.0, Ar), 7.95 (1H, d, J 7.0, Ar), 8.05-8.10 (1H, m, Ar), 8.11 (1H, d, J 4.9, β-H) 8.16-8.23 (1H, m, Ar), 8.25-8.38 (4H, m, Ar), 8.42 (1H, d, J 4.6, β-H), 8.47 (1H, d, 4.9, β-H), 8.98 (1H, d, J 5.0, β-H), 9.04 (1H, d, 4.6, β-H), 9.16 (1H, d, J 5.0, β-H); δ$_C$ (125 MHz; CDCl$_3$) 14.28 (CH$_3$), 14.33 (CH$_3$), 22.86 (CH$_2$), 22.95 (CH$_2$), 30.38 (CH$_2$), 30.46 (CH$_2$), 31.98 (CH$_2$), 32.09 (CH$_2$), 33.68 (CH$_2$), 35.48 (CH$_2$), 36.80 (CH$_2$), 38.38 (CH$_2$), 52.52 (OCH$_3$), 73.61 (β-C), 73.82 (β-C), 111.18 (meso-C), 113.40 (meso-C), 120.61 (meso-C), 122.36 (β-C), 123.73 (meso-C), 123.95 (β-C), 125.72 (β-C), 127.61 (β-C), 128.08 (Ar), 128.76 (Ar), 129.30 (Ar), 129.65 (Ar), 129.74 (Ar), 130.02 (β-C), 132.24 (Ar), 132.71 (β-C), 133.95 (Ar), 134.16 (Ar), 134.82 (α-C), 134.97 (α-C), 139.66 (α-C), 140.69 (α-C), 146.40 (Ar), 146.90 (Ar), 151.92 (α-C), 153.22 (α-C), 159.91 (α-C), 161.68 (α-C), 167.22 (CO$_2$CH$_3$), 167.46 (CO$_2$CH$_3$); m/z (EI) 780 ([M]$^+$, 21%), 762 ([M−H$_2$O], 61), 746 ([M−H$_2$OH]$^+$, 71), 690 ([M−H$_2$O—C$_5$H$_{11}$]$^+$, 51), 675 ([M-2 OH—C$_5$H$_{11}$]$^+$, 100), 604 ([M-2 OH-2 C$_5$H$_{11}$]$^+$, 30), 390 ([M]$^{2+}$, 8), 381 ([M−H$_2$O]$^{2+}$, 7), 373 ([M-2 OH]$^{2+}$, 7); m/z HRMS (ET) 780.3889 ([M]$^+$·, C$_{48}$H$_{52}$N$_4$O$_6^+$· requires 780.3881).

5,10-Dihexyl-17,18-dihydroxy-15,20-bis-(4-methoxycarbonylphenyl)-17,18-chlorin

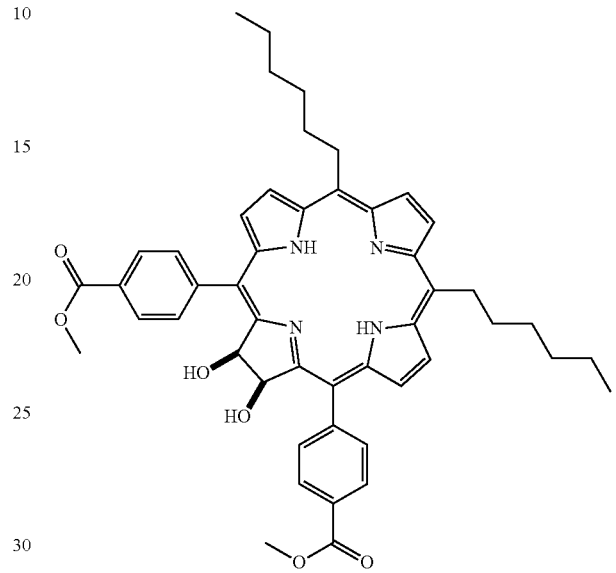

violet microcrystalline solid, mp 121° C.; λ$_{max}$ (CH$_2$Cl$_2$)/nm 409 (ε/dm$^3$ mol$^{-1}$ cm$^{-1}$ 163200), 428 (128300), 526sh (16300), 547 (19300), 593 (7700) and 645 (21000); δ$_H$ (500 MHz; CDCl$_3$) −1.53 (2H, s, NH), 0.93 (6H, t, J 7.3 Hz, 2×CH$_3$), 1.36-1.49 (8H, m, 4×CH$_2$), 1.73 (4H, m$_c$, 2×CH$_2$), 2.40 (4H, m$_c$, CH$_2$), 4.05 (6H, s, 2×OCH$_3$), 4.58-4.67 (4H, m, 2×CH$_2$), 6.10 (2H, s, β-H), 7.89 (2H, J 6.3, Ar), 8.08 (2H, J 6.3, Ar), 8.19 (2H, d, J 5.0, β-H), 8.29 (2H, d, J 6.3, Ar), 8.35 (2H, d, J 6.3, Ar), 9.12 (2H, d, J 5.0 Hz, β-H), 9.13 (2H, s, β-H); δ$_C$ (125 MHz; CDCl$_3$) 14.28 (CH$_3$), 22.86 (CH$_2$), 30.37 (CH$_2$), 32.00 (CH$_2$), 35.56 (CH$_2$), 38.27 (CH$_2$), 52.47 (OCH$_3$), 73.94 (β-C), 111.25 (meso-C), 123.83 (meso-C), 124.22 (β-C), 125.41 (β-C), 128.67 (Ar), 129.14 (Ar), 129.63 (Ar), 130.34 (β-C), 132.36 (Ar), 134.16 (Ar), 135.14 (α-C), 140.19 (α-C), 146.53 (Ar), 152.94 (α-C), 160.57 (α-C), 167.31 (CO$_2$CH$_3$); m/z (ESI) 781.3989 ([M+H]$^+$, C$_{48}$H$_{53}$N$_4$O$_6^+$ requires 781.3960).

3.3 Preparation of 7,8-dihydroxy-5,15-bis-(3-hydroxyphenyl)-10,20-bis-(tridecyl)-7,8-chlorin In a typical experiment, a solution of osmium tetroxide (36 mg, 0.14 mmol) in dichloromethane/pyridine 30% (4 ml) was added to a stirred solution of 5,15-bis-(3-hydroxyphenyl)-10,20-bis-(tridecyl)-porphyrin (80 mg, 0.09 mmol) in dichloromethane/pyridine 30% (6 ml). After stirring for 5 h a saturated solution of sodium bisulfite in water/methanol 1:1 (15 ml) was added and the mixture was stirred for 18 h. The reaction mixture was filtered through Celite and dried over sodium sulfate. The solvent was evaporated and the residue was purified by flash chromatography with dichloromethane/ethylacetate 90:10 as eluent, followed by recrystallization from dichloromethane/aqueous methanol. The first band from the column contained starting material (30 mg, 39%)

and the second band the title compound 7,8-dihydroxy-5,15-bis-(3-hydroxyphenyl)-10,20-bis-(tridecyl)-7,8-chlorin (35 mg, 44%).

7,8-Dihydroxy-5,15-bis-(3-hydroxyphenyl)-10,20-bis-(tridecyl)-7,8-chlorin

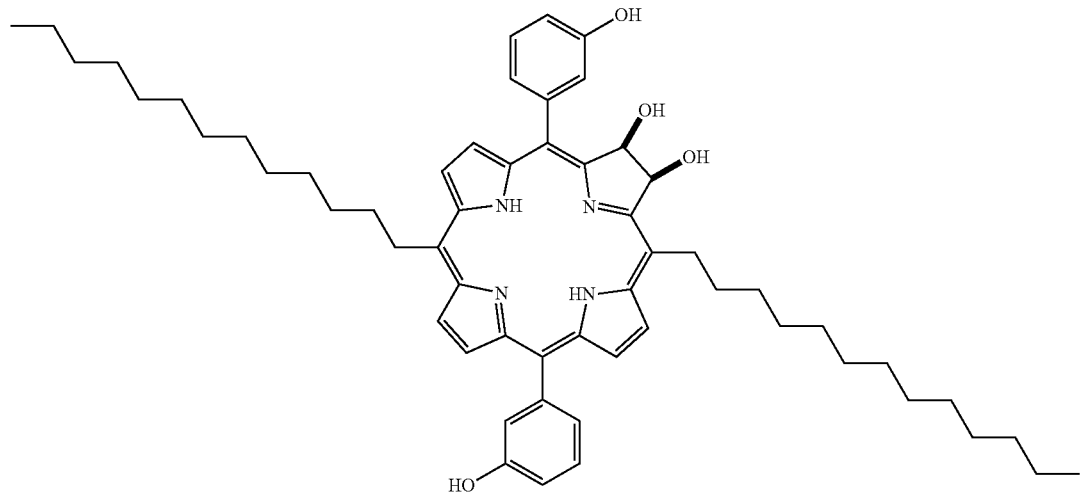 [SMILES: CCCCCCCCCCCCCc1c2nc(c(-c3cccc(O)c3)c3ccc([nH]3)c(CCCCCCCCCCCCC)c3nc(c(-c4cccc(O)c4)c4ccc1[nH]4)[C@@H](O)[C@H]3O)C=C2]

violet microcrystalline solid, mp 111-120° C.; $\delta_H$ (500 MHz; CDCl$_3$) −1.88 (1H, s, NH), −1.65 (1H, s, NH), 0.82-0.85 (6H, m, 2×CH$_3$), 1.22-1.34 (32H, m, 16×CH$_2$), 1.40-1.49 (4H, m, 2×CH$_2$), 1.67-1.74 (4H, m, 2×CH$_2$), 2.22-2.40 (4H, m, 2×CH$_2$), 4.35-4.41 (1H, m, HCH), 4.61-4.71 (3H, m, CH$_2$, HCH), 6.26-6.33 (1H, m, β-H), 6.50-6.53 (1H, m, β-H), 7.16-7.18 (1H, m, Ar), 7.25-7.28 (1H, m, Ar), 7.40-7.63 (6H, m, Ar), 8.35 (1H, d, J 4.8, β-H), 8.52 (1H, d, J 4.9, β-H), 8.75 (1H, d, 14.9, β-H), 9.14 (2H, d, J 4.9, β-H), 9.32 (1H, d, J 4.8, β-H); $\delta_C$ (125 MHz; CDCl$_3$) 13.5 (CH$_3$), 22.5 (CH$_2$), 28.9 (CH$_2$), 29.1 (CH$_2$), 29.2 (CH$_2$), 29.4 (CH$_2$), 29.5 (CH$_2$), 29.6 (CH$_2$), 29.7 (CH$_2$), 30.2 (CH$_2$), 30.5 (CH$_2$), 31.8 (CH$_2$), 34.5 (CH$_2$), 36.3 (CH$_2$), 38.1 (CH$_2$), 72.9 (β-C), 74.5 (β-C), 113.0 (meso-C), 114.4 (Ar), 114.7 (Ar), 121.4 (Ar), 121.7 (α-C), 122.4 (Ar), 124.1 (Ar), 124.4 (β-C), 125.8 (Ar), 127.6 (Ar), 128.3 (β-C), 129.2 (β-C), 132.9 (β-C), 134.1 (α-C), 135.2 (α-C), 139.4 (α-C), 140.9 (α-C), 143.8 (Ar), 151.8 (α-C), 153.4 (α-C), 155.8 (Ar); m/z (EI) 875 ([M−H$_2$O]$^+$., 37%), 856 ([M−2H$_2$O]$^+$., 13), 706 ([M−H$_2$O—C$_{12}$H$_{25}$]$^+$., 6).

3.4 Preparation of 17,18-dihydroxy-5,10-bis-(3-hydroxyphenyl)-15,20-bis-(tridecyl)-17,18-chlorin, 7,8-dihydroxy-5,20-bis-(3-hydroxyphenyl)-10,15-bis-(tridecyl)-7,8-chlorin and 7,8-dihydroxy-5,10-bis-(3-hydroxyphenyl)-15,20-bis-(tridecyl)-7,8-chlorin In a typical experiment, a solution of osmium tetroxide (76 mg, 0.30 mmol) in dichloromethane/pyridine 30% (8 ml) was added to a stirred solution of 5,10-Bis-(3-hydroxyphenyl)-15,20-bis-(tridecyl)-porphyrin (185 mg, 0.22 mmol) in dichloromethane/pyridine 30% (10 ml). After stirring for 5 h a saturated solution of sodium bisulfite in water/methanol 1:1 (20 ml) was added and the mixture was stirred for 18 h. The reaction mixture was filtered through Celite and dried over sodium sulfate. The solvent was evaporated and the residue was purified by repeated flash chromatography with dichloromethane/ethylacetate 90:10, 40:10 and dichloromethane/methanol 95:5 as eluent, followed by recrystallization from dichloromethane/aqueous methanol. The first band from the column contained starting material (19 mg, 10%), the second band the title compound 17,18-dihydroxy-5,10-bis-(3-hydroxyphenyl)-15,20-bis-(tridecyl)-17,18-chlorin (49 mg, 25%), the third band the title compound 7,8-dihydroxy-5,20-bis-(3-hydroxyphenyl)-10,15-bis-(tridecyl)-7,8-chlorin (47 mg, 24%) and the fourth band contained the title compound 7,8-dihydroxy-5,10-bis-(3-hydroxyphenyl)-15,20-bis-(tridecyl)-7,8-chlorin (25 mg, 13%).

17,18-Dihydroxy-5,10-bis-(3-hydroxyphenyl)-15,20-bis-(tridecyl)-17,18-chlorin

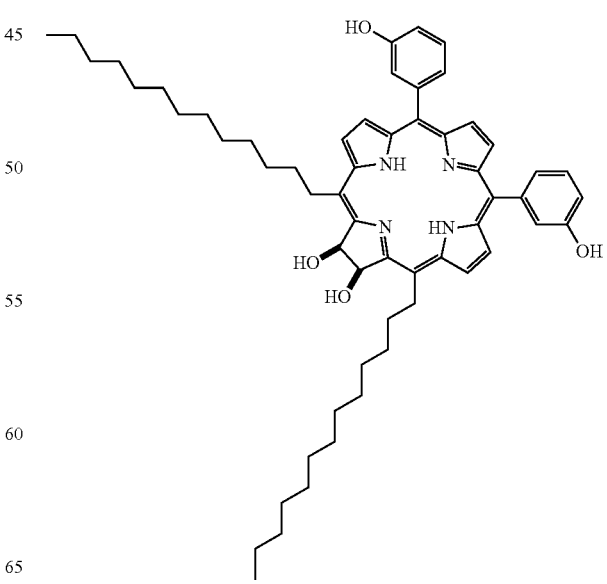

violet microcrystalline solid, mp 103° C.; $\delta_H$ (500 MHz; $(CD_3)_2SO$) −2.22 (2H, s, NH), 0.78 (6H, t, J 6.9 2×$CH_3$), 1.10-1.30 (32H, m, 16×$CH_2$), 1.35-1.43 (4H, m, 2×$CH_2$), 1.60-1.70 (4H, m, 2×$CH_2$), 2.08-2.25 (4H, m, 2×$CH_2$), 4.32-4.40 (2H, m, 2×HCH), 4.53-4.63 (2H, m, 2×HCH), 6.01 (2H, s, β-OH), 6.44 (2H, s, β-H), 7.15-7.20 (2H, m, Ar), 7.45-7.54 (6H, m, Ar), 8.39 (2H, s, β-H), 8.72 (2H, d, J 4.7, β-H), 9.19 (2H, d, J 4.7, β-H), 9.79 (2H, s, Ar—OH); $\delta_C$ (125 MHz; $(CD_3)_2SO$) 14.4 ($CH_3$), 22.6 ($CH_2$), 29.2 ($CH_2$), 29.5 ($CH_2$), 29.6 ($CH_2$), 30.5 ($CH_2$), 31.8 ($CH_2$), 33.4 ($CH_2$), 36.6 ($CH_2$), 73.3 (β-C), 113.4 (meso-C), 115.4 (Ar), 120.8 (meso-C), 122.9 β-C), 125.6 (Ar), 128.3 (Ar), 128.3 (β-C), 132.5 (β-C), 134.5 (α-C), 140.0 (α-C), 143.1 (Ar), 152.1 (α-C), 156.4 (Ar), 164.0 (α-C); m/z (EI) 892 ([M]$^+$., 5%), 874 ([M−$H_2O$]$^+$., 100), 858 ([M-2 OH)]$^+$., 31) 705 ([M−$H_2O$—$C_{12}H_{25}$]$^+$., 14).

7,8-Dihydroxy-5,20-bis-(3-hydroxyphenyl)-10,15-bis-(tridecyl)-7,8-chlorin

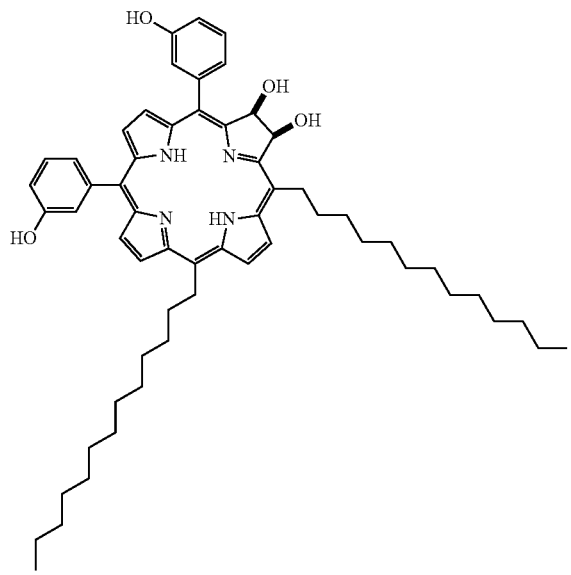 [SMILES: CCCCCCCCCCCCCc1c2nc(c(-c3cccc(O)c3)c3ccc([nH]3)c(-c3cccc(O)c3)c3nc(c(CCCCCCCCCCCCC)c4ccc1[nH]4)[C@H](O)[C@@H]3O)C=C2]

violet microcrystalline solid, mp 203-205° C.; $\delta_H$ (500 MHz; $(CD_3)_2SO$) −2.02 (1H, s, NH), −1.92 (1H, s, NH), 0.78-0.82 (6H, m, 2×$CH_3$), 1.12-1.46 (36H, m, 18×$CH_2$), 1.59-1.71 (4H, m, 2×$CH_2$), 2.10-2.25 (2H, m, $CH_2$), 2.26-2.32 (2H, m, $CH_2$), 4.35-4.41 (1H, m, HCH), 4.60-4.66 (1H, m, HCH), 4.67-4.73 (2H, m, $CH_2$), 5.31 (1H, s, β-OH), 5.81 (1H, s, β-OH), 6.05-6.11 (1H, m, β-H), 6.38-6.44 (1H, m, β-H), 7.05-7.07 (1H, m, Ar), 7.14-7.19 (1H, m, Ar), 7.25-7.56 (6H, m, Ar), 8.23 (1H, d, J 4.8, β-H), 8.43 (1H, d, J 4.6, β-H), 8.56 (1H, d, J 4.9, β-H), 9.17 (1H, β-H), 9.25 (1H, d, J 4.8, β-H), 9.54 (1H, d, J 4.9, β-H); $\delta_C$ (125 MHz; $(CD_3)_2SO$) 14.4 ($CH_3$), 14.5 ($CH_3$), 22.6 ($CH_2$), 29.2 ($CH_2$), 29.5 ($CH_2$), 29.6 ($CH_2$), 29.7 ($CH_2$), 31.8 ($CH_2$), 38.5 ($CH_2$), 73.3 (β-C), 74.6 (β-C), 122.8 (β-C), 124.8 (β-C), 126.5 (β-C), 128.3 (β-C) 130.6 (β-C), 132.8 (β-C), 134.6 (α-C), 143.1 (Ar), 151.7 (α-C), 152.6 (α-C), 164.1 (α-C); m/z (EI) 874 ([M−$H_2O$]$^+$., 20%), 705 ([M−$H_2O$—$C_{12}H_{25}$]$^+$., 9).

7,8-Dihydroxy-5,10-bis-(3-hydroxyphenyl)-15,20-bis-(tridecyl)-7,8-chlorin

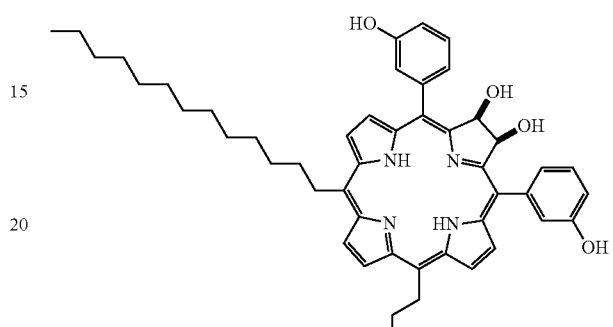

violet microcrystalline solid, mp 137-141° C.; $\delta_H$ (500 MHz; $(CD_3)_2CO$) −1.56 (2H, s, NH), 0.83-0.86 (6H, m, 2×$CH_3$), 1.24-1.35 (32H, m, 16×$CH_2$), 1.45-1.51 (4H, m, 2×$CH_2$), 1.72-1.78 (4H, m, 2×$CH_2$), 2.42 (4H, $m_c$, 2×$CH_2$), 4.70-4.80 (4H, m, 2×$CH_2$), 6.18-6.28 (2H, m, β-H), 7.12-7.15 (2H, m, Ar), 7.30-7.63 (6H, m, Ar), 8.37 (2H, d, J 4.8, β-H), 8.59 (2H, s, Ar—OH), 9.26 (2H, s, β-H), 9.36 (2H, J 4.8, β-H); $\delta_C$ (125 MHz; $(CD_3)_2CO$) 13.5 ($CH_3$), 22.5 ($CH_2$), 28.9 ($CH_2$), 29.1 ($CH_2$), 29.2 ($CH_2$), 29.3 ($CH_2$), 29.4 ($CH_2$), 29.5 ($CH_2$), 29.6 ($CH_2$), 30.2 ($CH_2$), 31.8 ($CH_2$), 34.9 ($CH_2$), 38.2 ($CH_2$), 73.9 (β-C), 112.7 (meso-C), 122.7 (meso-C), 124.1 (β-C), 125.1 (β-C), 130.1 (β-C), 134.8 (α-C), 140.5 (α-C), 143.1 (Ar), 152.6 (α-C), 162.6 (α-C); m/z (EI) 874 ([M−$H_2O$]$^+$., 1%), 705 ([M−$H_2O$—$C_{12}H_{25}$]$^+$., 1).

3.5 Preparation of 5,10,15-trihexyl-7,8-dihydroxy-20-(4-methoxycarbonylphenyl)-7,8-chlorin and 5,10,15-trihexyl-17,18-dihydroxy-20-(4-methoxycarbonylphenyl)-17,18-chlorin In a typical experiment, a solution of osmium tetroxide (100 mg, 0.39 mmol) in dichloromethane/pyridine 30% (10 ml) was added to a stirred solution of 5,10,15-trihexyl-20-(4-methoxycarbonylphenyl)-porphyrin (212 mg, 0.30 mmol) in dichloromethane/pyridine 30% (45 ml). After stirring for 13 days a saturated solution of sodium bisulfite in water/methanol 1:1 (40 ml) was added and the mixture was stirred for 18 h. The reaction mixture was filtered through Celite and dried over sodium sulfate. The solvent was evaporated and the residue was purified by repeated flash chromatography with dichloromethane/ethylacetate 95:5 as eluent, followed by recrystallization from dichloromethane/aqueous methanol. The first band from the column contained starting material (103 mg, 49%), the second band the title compound 5,10,15-trihexyl-7,8-dihydroxy-20-(4-methoxycarbonylphenyl)-7,8-chlorin (48 mg, 22%) and the third band the title compound 5,10,15-trihexyl-17,18-dihydroxy-20-(4-methoxycarbonylphenyl)-17,18-chlorin (34 mg, 15%).

5,10,15-Trihexyl-7,8-dihydroxy-20-(4-methoxycarbonylphenyl)-7,8-chlorin

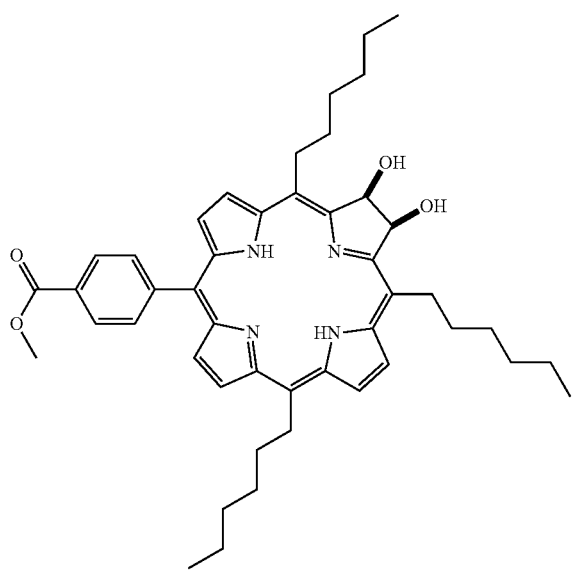 [SMILES: CCCCCCc1c2nc(c(-c3ccc(C(=O)OC)cc3)c3ccc([nH]3)c(CCCCCC)c3nc(c(CCCCCC)c4ccc1[nH]4)[C@H](O)[C@@H]3O)C=C2]

violet microcrystalline solid, mp 109-111° C.; $\lambda_{max}$ ($CH_2Cl_2$)/nm 410 ($\epsilon$/dm$^3$ mol$^{-1}$ cm$^{-1}$ 146100), 430 (121700), 527 (12400), 556 (16300), 596 (7400), and 649 (14900); $\delta_H$ (500 MHz; CDCl$_3$) −2.15 (2H, br s, NH), 0.90-0.94 (6H, m, 2×CH$_3$), 0.95 (3H, t, J 7.0, CH$_3$), 1.31-1.47 (12H, m, 6×CH$_2$), 1.59-1.71 (6H, m, 3×CH$_2$), 1.97-2.12 (4H, m, 2×CH$_2$), 2.17-2.29 (2H, m, CH$_2$), 4.02-4.37 (9H, m, 3×CH$_2$, OCH$_3$), 6.14-6.17 (2H, m, β-H), 8.11-8.22 (2H, br m, Ar), 8.38 (2H, d, J 8.3 Hz, Ar), 8.42 (1H, d, J 4.4, β-H), 8.59 (1H, d, J 4.8, β-H), 8.61 (1H, d, J 4.7, β-H), 8.73 (1H, d, J 4.7, β-H), 8.94 (1H, d, J 4.8, β-H), 8.99 (1H, d, J 4.4, β-H); $\delta_C$ (125 MHz; CDCl$_3$) 14.29 (CH$_3$), 14.33 (CH$_3$), 22.86 (CH$_2$), 22.89 (CH$_2$), 22.94 (CH$_2$), 30.33 (CH$_2$), 30.34 (CH$_2$), 30.38 (CH$_2$), 31.95 (CH$_2$), 32.01 (CH$_2$), 32.03 (CH$_2$), 33.24 (CH$_2$), 33.59 (CH$_2$), 36.57 (CH$_2$), 36.68 (CH$_2$), 38.09 (CH$_2$), 52.56 (OCH$_3$), 73.33 (β-C), 73.83 (β-C), 112.20 (meso-C), 112.24 (meso-C), 119.32 (meso-C), 121.83 (β-C), 122.24 (meso-C), 122.43 (β-C), 124.87 (β-C), 127.97 (Ar), 128.01 (β-C), 129.52 (Ar), 129.67 (β-C), 132.61 (β-C), 134.19 (Ar), 134.61 (α-C), 139.42 (α-C), 140.38 (α-C), 147.34 (Ar), 151.53 (α-C), 152.94 (α-C), 159.70 (α-C), 161.12 (α-C), 167.56 (CO$_2$CH$_3$); m/z (ESI) 731.4485 ([M+H]$^+$ C$_{46}$H$_{59}$N$_4$O$_4^+$ requires 731.4531).

5,10,15-Trihexyl-17,18-dihydroxy-20-(4-methoxycarbonylphenyl)-17,18-chlorin

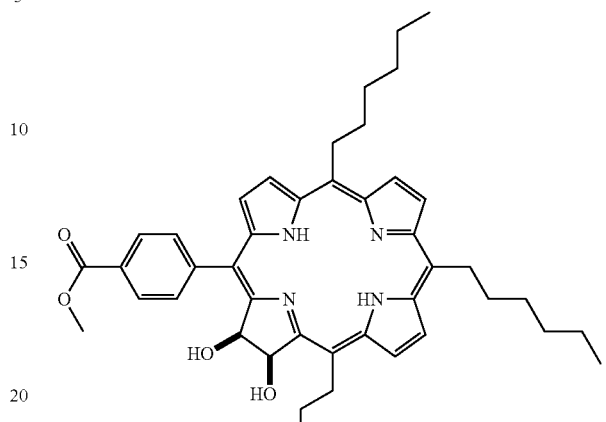

violet microcrystalline solid; $\lambda_{max}$ (CH$_2$CH$_2$)/nm 409 ($\epsilon$/dm$^3$ mol$^{-1}$ cm$^{-1}$ 209900), 430 (167300), 527 (17900), 554 (22200), 595 (10300) and 647 (19800); $\delta_H$ (500 MHz; CDCl$_3$) −1.86 (2H, br s, NH), 0.92-0.97 (9H, m, 3×CH$_3$), 1.34-1.51 (12H, m, 6×CH$_2$), 1.67-1.76 (6H, m, 3×CH$_2$), 2.07-2.29 (2H, m, CH$_2$), 2.34-2.42 (4H, m, 2×CH$_2$), 4.06 (3H, s, OCH$_3$), 4.21-4.28 (1H, m, HCH), 4.34-4.40 (1H, m, HCH), 4.52-4.59 (4H, m, 2×CH$_2$), 6.01 (1H, d, J 7.2, β-H), 6.26 (1H, d, J 7.2, β-H), 7.79-7.90 (2H, br m, Ar), 8.08 (1H, d, J 5.0, β-H), 8.23-8.33 (2H, br m, Ar), 8.91 (1H, d, J 5.0, β-H), 9.05 (1H, d, J 5.0, β-H), 9.09 (2H, s, β-H), 9.13 (1H, d, J 7.2, β-H); $\delta_C$ (125 MHz; CDCl$_3$) 14.30 (CH$_3$), 14.33 (CH$_3$), 22.87 (CH$_2$), 22.91 (CH$_2$), 22.95 (CH$_2$), 30.37 (CH$_2$), 30.42 (CH$_2$), 32.00 (CH$_2$), 32.01 (CH$_2$), 32.09 (CH$_2$), 33.34 (CH$_2$), 35.30 (CH$_2$), 35.58 (CH$_2$), 36.61 (CH$_2$), 38.15 (CH$_2$), 38.33 (CH$_2$), 52.51 (OCH$_3$), 73.52 (β-C), 73.85 (β-C), 110.27 (meso-C), 112.26 (meso-C), 121.92 (α-C), 122.91 (meso-C), 122.93 (meso-C), 123.60 (β-C), 124.83 (β-C), 125.67 (β-C), 128.65 (Ar), 129.18 (Ar), 129.54 (Ar), 129.92 (β-C), 130.21 (β-C), 132.34 (Ar), 133.90 (Ar), 134.41 (α-C), 135.08 (α-C), 139.21 (α-C), 140.87 (α-C), 146.75 (Ar), 152.35 (α-C), 152.76 (α-C), 158.99 (α-C), 161.59 (α-C), 167.30 (CO$_2$CH$_3$); m/z (EI) 730 ([M]$^+$, 29%), 712 [M−H$_2$O]$^+$, 100), 697 ([M−2 OH]$^+$, 42), 641 ([M−H$_2$O—C$_5$H$_{11}$]$^+$, 57), 623 ([M-2 OH—C$_5$H$_{11}$]$^+$, 71); m/z HRMS (EI) 730.4454 ([M]$^+$., C$_{46}$H$_{58}$N$_4$O$_4^+$., requires 730.4453).

Example 4

Preparation of Unsymmetrical Carboxy-Substituted Chlorins 4.1 Preparation of 5,15-bis-(4-carboxyphenyl)-10,20-dihexyl-7,8-dihydroxy-7,8-chlorin In a typical experiment, a solution of KOH (100 mg, 1.8 mmol) in methanol (1 ml) was added to a stirred solution of 5,15-dihexyl-7,8-dihydroxy-10,20-bis-(4-methoxycarbonylphenyl)-7,8-chlorin (20 mg, 0.016 mmol) in THF (3 ml) and the reaction mixture was stirred for 2 d. Water (50 ml) and hydrochloric acid were then added until the pH was adjusted to 4-6. The aqueous layer was extracted with dichloromethane (2×100 ml) and the organic layer was separated, washed with water until neutral and dried over sodium sulfate. The solvent was evaporated and the title compound 5,15-bis-(4-carboxyphenyl)-10,20-dihexyl-7,8-dihydroxy-7,8-chlorin was obtained after recrystallization from dichloromethane/aqueous methanol (18 mg, 92%).

5,15-Bis-(4-carboxyphenyl)-10,20-dihexyl-7,8-dihydroxy-7,8-chlorin

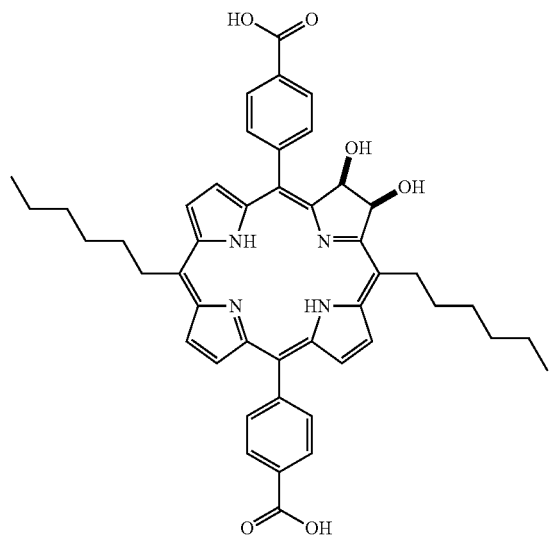 [SMILES: CCCCCCc1c2nc(c(-c3ccc(C(=O)O)cc3)c3ccc([nH]3)c(CCCCCC)c3nc(c(-c4ccc(C(=O)O)cc4)c4ccc1[nH]4)[C@@H](O)[C@H]3O)C=C2]

violet microcrystalline solid, mp>300° C.; $\lambda_{max}$ ((CH$_3$)$_2$CO)/nm 407 ($\epsilon$/dm$^3$ mol$^{-1}$ cm$^{-1}$ 154700), 427 (130300), 521 (13600), 548 (15300), 594 (6500) and 646 (17600); $\delta_H$ (500 MHz; (CD$_3$)$_2$SO) −2.05 (1H, s, NH), −1.85 (1H, s, NH), 0.84 (3H, t, J 7.3 Hz, CH$_3$), 0.91 (3H, t, J 7.3, CH$_3$), 1.24-1.48 (8H, m, 4×CH$_2$), 1.64-1.67 (2H, m, CH$_2$), 1.69-1.75 (2H, m, CH$_2$), 2.12-2.23 (2H, m, CH$_2$), 2.25-2.31 (2H, m, CH$_2$), 4.35-4.41 (1H, m, HCH), 4.57-4.64 (1H, m, HCH), 4.66-4.72 (2H, m, CH$_2$), 5.40 (1H, br s, OH), 5.86 (1H, br s, OH), 6.09 (1H, d, J 6.9, β-H), 6.40 (1H, d, J 6.9, β-H), 8.02-8.35 (10H, m, 8×Ar, 2×β-H), 8.64 (1H, d, J 5.0, β-H), 9.19 (1H, d, J 4.7, β-H), 9.24 (1H, d, J 5.0, β-H), 9.45 (1H, d, J 5.2, β-H); $\delta_C$ (125 MHz; (CD$_3$)$_2$SO) 13.93 (CH$_3$), 14.02 (CH$_3$), 22.10 (CH$_2$), 22.23 (CH$_2$), 29.30 (CH$_2$), 29.67 (CH$_2$), 31.27 (CH$_2$), 31.36 (CH$_2$), 33.88 (CH$_2$), 111.99 (meso-C), 113.10 (meso-C), 119.32 (meso-C), 122.64 (β-C), 123.87 (β-C), 127.79 (Ar), 128.23 (β-C), 132.40 (β-C), 133.59 (Ar), 146.10 (Ar), 146.46 (Ar) 167.50 (CO$_2$H), 167.67 (CO$_2$H); m/z (ESI) 753.3664 ([M+H]$^+$, C$_{46}$H$_{49}$N$_4$O$_6$$^+$ requires 753.3647).

4.2 Preparation of 5,20-bis-(4-carboxyphenyl)-10,15-dihexyl-7,8-dihydroxy-7,8-chlorin In a typical experiment, a solution of KOH (200 mg, 3.6 mmol) in methanol (1 ml) was added to a stirred solution of 5,20-dihexyl-7,8-dihydroxy-10,15-bis-(4-methoxycarbonylphenyl)-7,8-chlorin (35 mg, 0.045 mmol) in THF (3 ml) and the reaction mixture was stirred for 2 d. Water (50 ml) and hydrochloric acid were then added until the pH was adjusted to 4-6. The aqueous layer was extracted with dichloromethane (2×100 ml) and the organic layer was separated, washed with water until neutral and dried over sodium sulfate. The solvent was evaporated and the title compound 5,20-bis-(4-carboxyphenyl)-10,15-dihexyl-7,8-dihydroxy-7,8-chlorin was obtained after recrystallization from dichloromethane/aqueous methanol (31 mg, 91%).

5,20-Bis-(4-carboxyphenyl)-10,15-dihexyl-7,8-dihydroxy-7,8-chlorin

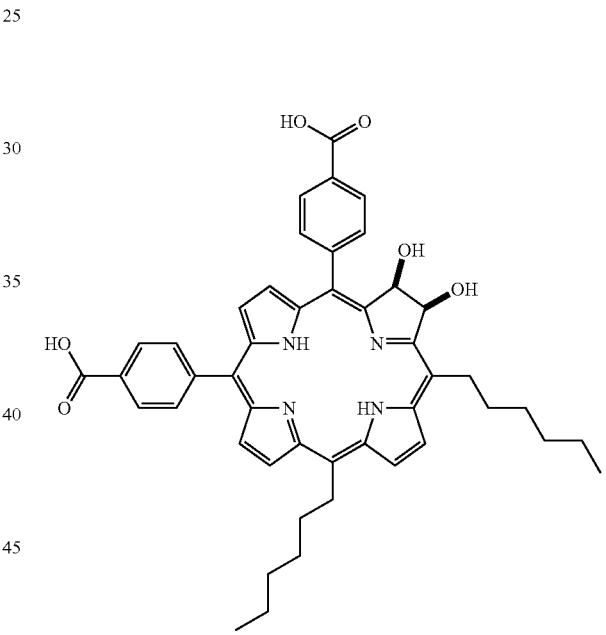

violet microcrystalline solid, mp>300° C.; $\lambda_{max}$ ((CH$_3$)$_2$CO)/nm 407 ($\epsilon$/dm$^3$ mol$^{-1}$ cm$^{-1}$ 122800), 427 (96000), 523 (10100), 548 (11500), 595 (4600) and 646 (13900); $\delta_H$ (500 MHz; (CD$_3$)$_2$CO) −1.88 (1H, s, NH), −1.74 (1H, s, NH), 0.91 (3H, t, J 7.3 Hz, CH$_3$), 0.96 (3H, t, J 7.3, CH$_3$), 1.34-1.56 (8H, m, 4×CH$_2$), 1.75-1.85 (4H, m, 2×CH$_2$), 2.28-2.46 (4H, m, 2×CH$_2$), 4.44-4.50 (1H, m, HCH), 4.65-4.72 (1H, m, HCH), 4.77 (2H, m$_c$, CH$_2$), 6.33 (1H, d, J 7.0, β-H), 6.53 (1H, d, J 7.0, β-H), 8.24 (1H, d, J 4.9, β-H), 8.00-8.40 (8H, br m, Ar), 8.42 (1H, d, J 4.5, β-H), 8.56 (1H, d, J 4.9, β-H), 9.21 (1H, d, J 4.5, β-H), 9.30 (1H, d, J 5.0, β-H), 9.56 (1H, d, J 5.0, β-H); $\delta_C$ (125 MHz; (CD$_3$)$_2$SO) 14.00 (CH$_3$), 14.10 (CH$_3$), 22.19 (CH$_2$), 22.33 (CH$_2$), 29.38 (CH$_2$), 29.76 (CH$_2$), 31.33 (CH$_2$), 31.44 (CH$_2$), 32.86 (CH$_2$), 34.39

(CH$_2$), 36.16 (CH$_2$), 38.12 (CH$_2$), 72.91 (β-C), 73.13 (β-C), 111.93 (meso-C), 113.17 (meso-C), 119.45 (meso-C), 122.66 (β-C), 124.10 (β-C), 126.43 (β-C), 127.44 (β-C), 127.92 (Ar), 129.52 (Ar), 130.20 (β-C), 132.11 (β-C), 133.76 (α-C), 133.87 (Ar), 134.29 (α-C), 139.06 (α-C), 140.04 (α-C), 145.84 (Ar), 146.22 (Ar), 150.78 (α-C), 152.25 (α-C), 163.07 (α-C), 163.91 (α-C), 167.53 (CO$_2$H), 167.71 (CO$_2$H); m/z (ESI) 753.3637 ([M+H]$^+$, C$_{46}$H$_{49}$N$_4$O$_6$ requires 753.3647).

4.3 Preparation of 5-(4-carboxyphenyl)-10,15,20-trihexyl-17,18-dihydroxy-17,18-chlorin In a typical experiment, a solution of KOH (100 mg, 1.8 mmol) in methanol (0.5 ml) was added to a stirred solution of 5,10,15-trihexyl-7,8-dihydroxy-20-(4-methoxycarbonylphenyl)-7,8-chlorin (12 mg, 0.016 mmol) in THF (2 ml) and the reaction mixture was stirred for 2 d. Water (50 ml) and hydrochloric acid were then added until the pH was adjusted to 4-6. The aqueous layer was extracted with dichloromethane (2×100 ml) and the organic layer was separated, washed with water until neutral and dried over sodium sulfate. The solvent was evaporated and the title compound 5-(4-carboxyphenyl)-10,15,20-trihexyl-17,18-dihydroxy-17,18-chlorin was obtained after recrystallization from dichloromethane/aqueous methanol (10 mg, 87%).

5-(4-Carboxyphenyl)-10,15,20-trihexyl-17,18-dihydroxy-17,18-chlorin

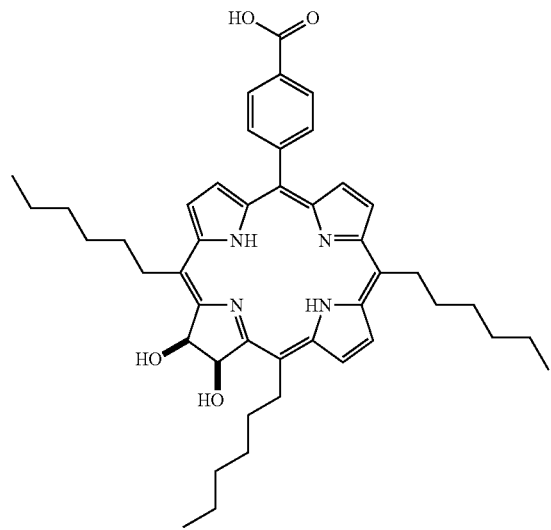 [SMILES: CCCCCCc1c2nc(c(-c3ccc(C(=O)O)cc3)c3ccc([nH]3)c(CCCCCC)c3nc(c(CCCCCC)c4ccc1[nH]4)[C@@H](O)[C@H]3O)C=C2]

violet microcrystalline solid, mp 134° C.; λ$_{max}$ ((CH$_3$)$_2$CO)/nm 408 (ε/dm$^3$ mol$^{-1}$ cm$^{-1}$ 88600), 428 (73300), 526 (8500), 553 (9200), 595 (4300) and 649 (7400); δ$_H$ (500 MHz; (CD$_3$)$_2$CO) −1.98 (1H, s, NH), −1.96 (1H, s, NH), 0.88-0.98 (9H, m, 3×CH$_3$), 1.33-1.55 (12H, m, 6×CH$_2$), 1.73-1.85 (6H, m, 3×CH$_2$), 2.20-2.45 (6H, m, 3×CH$_2$), 4.38-4.47 (2H, m, CH$_2$), 4.60-4.67 (2H, m, CH$_2$), 4.75 (2H, m$_c$, CH$_2$), 5.30 (1H, br s, COOH), 6.57 (2H, s, β-H), 8.19 (2H, d, J 8.1 Hz, Ar), 8.38 (1H, d, J 4.5, β-H), 8.41 (2H, d, J 8.1, Ar), 8.64 (1H, d, J 4.9, β-H), 9.16-9.18 (2H, m, β-H), 9.24 (1H, d, J 5.0, β-H), 9.49 (1H, d, J 5.0, β-H); δ$_C$ (125 MHz; (CD$_3$)$_2$CO) 14.37 (CH$_3$), 14.44 (CH$_3$), 14.47 (CH$_3$), 23.40 (CH$_2$), 23.50 (CH$_2$), 23.54 (CH$_2$), 30.77 (CH$_2$), 31.04 (CH$_2$), 31.09 (CH$_2$), 32.64, (CH$_2$), 32.71 (CH$_2$), 32.74 (CH$_2$), 34.12 (CH$_2$), 34.49 (CH$_2$), 35.54 (CH$_2$), 37.24 (CH$_2$), 37.37 (CH$_2$), 39.06 (CH$_2$), 74.14 (β-C), 74.28 (β-C), 113.62 (meso-C), 113.70 (meso-C), 119.70 (meso-C), 122.71 (meso-C), 123.05 (β-C), 123.13 (β-C), 126.16 (β-C), 128.42 (β-C), 128.88 (Ar), 130.50 (β-C), 130.79 (α-C), 133.08 (β-C), 134.83 (Ar), 135.70 (α-C), 140.53 (α-C), 141.03 (α-C), 148.04 (Ar), 152.14 (α-C), 153.83 (α-C), 163.12 (α-C), 164.13 (α-C), 167.87 (CO$_2$H); m/z (ESI) 717.4399 ([M+H]$^+$ C$_{45}$H$_{57}$N$_4$O$_4$$^+$ requires 717.4374).

4.4 Preparation of 5-(4-carboxyphenyl)-10,15,20-trihexyl-7,8-dihydroxy-7,8-chlorin In a typical experiment, a solution of KOH (200 mg, 3.6 mmol) in methanol (1 ml) was added to a stirred solution of 5,10,15-trihexyl-17,18-dihydroxy-20-(4-methoxycarbonylphenyl)-17,18-chlorin (25 mg, 0.034 mmol) in THF (3 ml) and the reaction mixture was stirred for 2 d. Water (50 ml) and hydrochloric acid were then added until the pH was adjusted to 4-6. The aqueous layer was extracted with dichloromethane (2×100 ml) and the organic layer was separated, washed with water until neutral and dried over sodium sulfate. The solvent was evaporated and the title compound 5-(4-carboxyphenyl)-10,15,20-trihexyl-7,8-dihydroxy-7,8-chlorin was obtained after recrystallization from dichloromethane/aqueous methanol (22 mg, 90%).

5-(4-Carboxyphenyl)-10,15,20-trihexyl-7,8-dihydroxy-7,8-chlorin

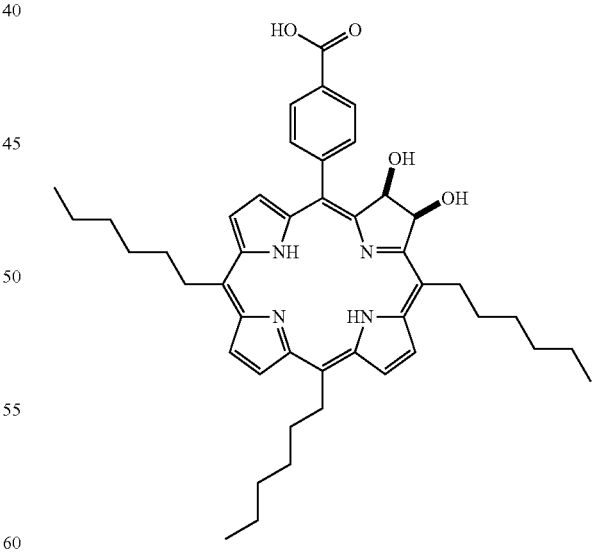

violet microcrystalline solid, mp 128-133° C.; λ$_{max}$ ((CH$_3$)$_2$CO)/nm 404 (ε/dm$^3$ mol$^{-1}$ cm$^{-1}$ 152200), 428 (114600), 525 (13300), 550 (15900), 595 (6600) and 647 (18200); δ$_H$ (500 MHz; (CD$_3$)$_2$CO) −1.78 (1H, s, NH), −1.59 (1H, s, NH), 0.87-0.96 (9H, m, 3×CH$_3$), 1.30-1.53 (12H, m, 6×CH$_2$), 1.68-1.80 (6H, m, 3×CH$_2$), 2.18-2.27 (1H, m, HCH), 2.29-2.42 (5H, m, 2×CH$_2$, HCH), 4.32-4.82 (1H, m, HCH), 4.54-4.60 (1H, m, HCH), 4.61-4.72 (4H, m, 2×CH$_2$), 6.17 (1H, d, J 7.1 β-H), 6.40 (1H, d, J 7.1 β-H), 7.89-7.95 (1H, br m, Ar), 8.11-8.16 (1H, m, Ar), 8.17 (1H, d, J 4.9, β-H), 8.22-8.36 (2H, br m, Ar), 9.14 (1H, d, J 5.0, β-H), 9.16 (1H, β-H), 9.18 (1H, d, J 4.7, β-H), 9.26 (1H, d, J 4.9, β-H), 9.41 (1H, d, J 5.0, β-H); δ$_C$ (125 MHz; (CD$_3$)$_2$CO) 14.37 (CH$_3$), 14.40 (CH$_3$), 14.46 (CH$_3$), 23.38 (CH$_2$), 23.42 (CH$_2$), 23.51 (CH$_2$), 30.73 (CH$_2$), 30.79 (CH$_2$), 31.05 (CH$_2$), 32.62, (CH$_2$), 32.63 (CH$_2$), 32.72 (CH$_2$), 33.93 (CH$_2$), 35.48 (CH$_2$), 35.82 (CH$_2$), 37.16 (CH$_2$), 38.92 (CH$_2$), 39.12 (CH$_2$), 73.88 (β-C), 74.55 (β-C), 112.13 (mesa-C), 113.27 (meso-C), 122.71 (β-C), 122.93 (meso-C), 122.96 (meso-C), 124.48 (β-C), 125.68 (β-C), 126.56 (β-C), 130.22 (α-C), 130.67 (β-C), 130.98 (β-C), 135.07 (α-C), 135.70 (α-C), 140.12 (α-C), 141.49 (α-C), 148.03 (Ar), 153.09 (α-C), 153.50 (α-C), 162.07 (α-C), 164.25 (α-C), 168.01 (CO$_2$H); m/z (ESI) 717.4356 ([M+H]$^+$ C$_{45}$H$_{57}$N$_4$O$_4^+$ requires 717.4374).

Example 5

Preparation of Porphyrins Containing Carbohydrate Moieties

5 Preparation of 5,15-dihexyl-10,20-bis-(3-β-D-acetoglucosylphenyl)-porphyrin and 5,10-dihexyl-15,20-bis-(3-β-D-acetoglucosylphenyl)-porphyrin In a typical experiment, dry dichloromethane (528 ml) was placed in a three-necked flask equipped with a magnetic stirrer and argon gas inlet. After pyrrole (528 μl, 7.62 mmol), heptanal (560 μl, 3.96 mmol) and tetraacetyl-β-D-glucopyranosyloxy-benzaldehyde (600 mg, 1.32 mmol) were added, the flask was shielded from ambient light and TFA (408 μl, 5.28 mmol) was added and the reaction mixture was stirred at room temperature for 18 h. Then, DDQ (898 mg, 3.96 mmol) suspended in dry dichloromethane (30 ml) was added. After further stirring for 1 h, triethylamine (1 ml) was added. To remove polymeric by-products, the reaction mixture was filtered through silica gel. The solvent was evaporated and purification was achieved via repeated flash chromatography with hexane/ethylacetate 60:40 and dichloromethane/ethylacetate 90:10 as eluent, followed by recrystallization from dichloromethane/methanol The first band from the column contained 5,10,15,20-tetrahexyl-porphyrin (51 mg, 8%), the second band 5,10,15-trihexyl-20-bis-(3-β-D-acetoglucosylphenyl)-porphyrin (145 mg, 11%), the third band the title compound 5,15-dihexyl-10,20-bis-(3-β-D-acetoglucosylphenyl)-porphyrin (33 mg, 4%) and the fourth band contained the title compound 5,10-dihexyl-15,20-bis-(3-β-D-acetoglucosylphenyl)-porphyrin (57 mg, 7%).

5,15-Dihexyl-10,29-bis-(3-β-D-acetoglucosylphenyl)-porphyrin

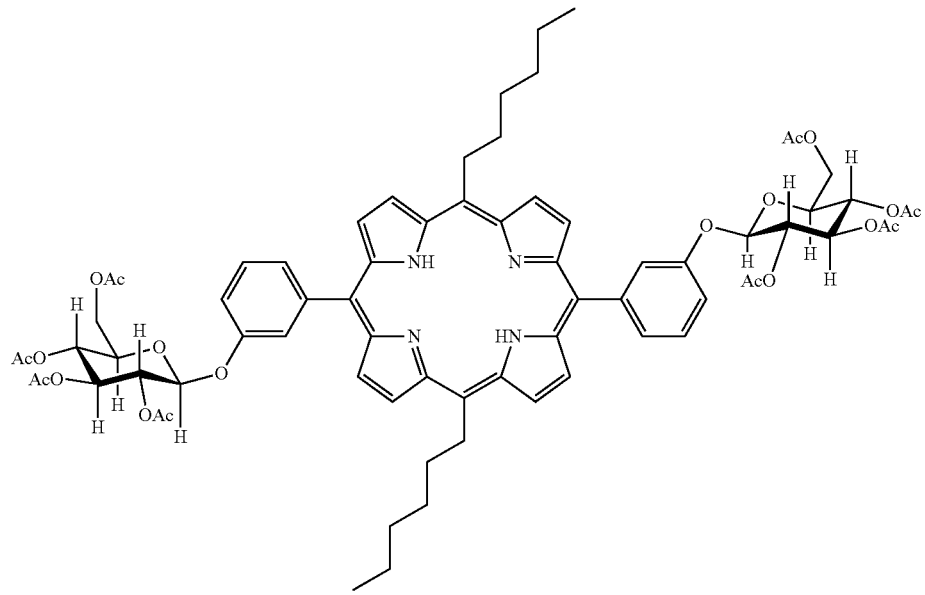

violet microcrystalline solid, δ$_H$ (500 MHz; CDCl$_3$) −2.72 (2H, s, NH), 0.91-0.96 (6H, m, 2×CH$_3$), 1.31-1.33 (6H, m, Ac), 1.36-1.43 (4H, m, 2×CH$_2$), 1.48-1.56 (4H, m, 2×CH$_2$), 1.77-1.84 (4H, m, 2×CH$_2$), 1.98 (6H, s, Ac), 2.04 (6H, s, Ac), 2.11 (6H, s, Ac), 2.49-2.55 (4H, m, 2×CH$_2$), 3.76-3.81 (2H, m, H-5 'ose'), 4.03-4.07 (2H, m, H-6 'ose') 4.14-4.18 (2H, m, H-6 'ose'), 4.94-5.00 (4H, m, 2×CH$_2$), 5.15-5.20 (2H, m, H-4 'ose'), 5.31-5.34 (2H, m, H-2/3 'ose'), 5.35-5.37 (2H, m, H-1 'ose'), 5.39-5.42 (2H, m, H-2/3 'ose'), 7.43-7.46 (2H, m, Ar), 7.66-7.69 (2H, m, Ar), 7.84-7.87 (2H, m, Ar), 7.92-7.95 (2H, m, Ar), 8.89 (4H, d, J 4.7, β-H), 9.43-9.46 (4H, m, β-H); δ$_C$ (125 MHz; CDCl$_3$) 14.23 (CH$_3$), 19.96 (COCH$_3$), 20.60 (COCH$_3$), 20.69 (COCH$_3$), 20.81 (COCH$_3$), 22.82 (CH$_2$), 30.31 (CH$_2$), 31.99 (CH$_2$), 35.42 (CH$_2$), 38.88 (CH$_2$), 61.99 (C-6 'ose'), 68.38 (C-4 'ose'), 71.40 (C-2/3 'ose'), 72.26 (C-5 'ose'), 72.89 (C-2/3 'ose'), 99.38 (C-1 'ose'), 116.71 (Ar), 118.10 (meso-C), 120.21 (meso-C), 122.77 (Ar). 127.67 (Ar), 128.07 (β-C), 129.94 (Ar), 131.70 (β-C), 144.31 (Ar), 155.34 (Ar), 169.44 (2×COCH$_3$), 170.30 (COCH$_3$), 170.45 (COCH$_3$); m/z (ESI) 1323.5 ([M+H]$^+$ C$_{72}$H$_{83}$N$_4$O$_{20}^+$ requires 1323.6).

5,10-Dihexyl-15,20-bis-(3-β-D-acetoglucosylphenyl)-porphyrin

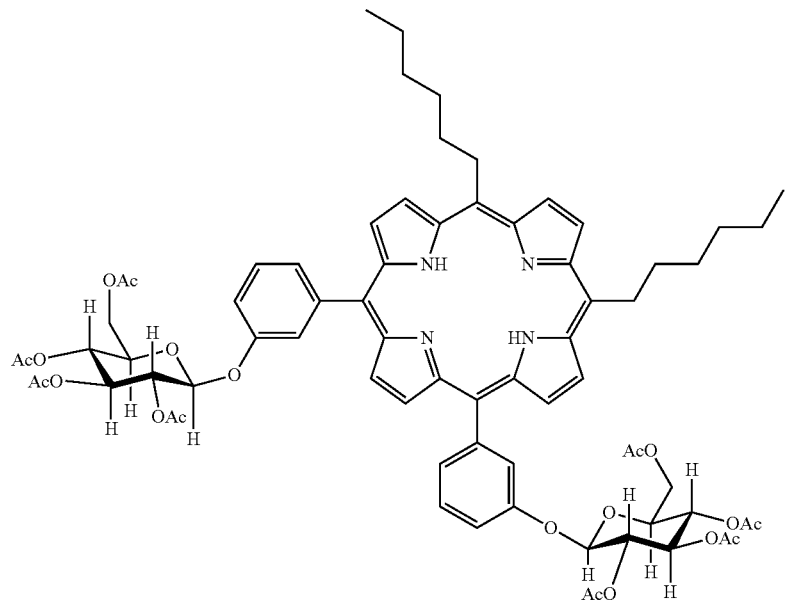

violet microcrystalline solid, $\delta_H$ (500 MHz; CDCl$_3$) −2.71 (2H, s, NH), 0.95-0.98 (6H, m, 2×CH$_3$), 1.32-1.38 (6H, m, Ac), 1.40-1.47 (4H, m, 2×CH$_2$), 1.52-1.59 (4H, m, 2×CH$_2$), 1.82-1.89 (4H, m, 2×CH$_2$), 1.98-2.01 (6H, m, Ac), 2.04-2.05 (6H, m, Ac), 2.10-2.12 (6H, m, Ac), 2.52-2.61 (4H, m, 2×CH$_2$), 3.75-3.84 (2H, m, H-5 'ose'), 4.02-4.07 (2H, m, H-6 'ose') 4.14-4.21 (2H, m, H-6 'ose'), 5.00-5.04 (4H, m, 2×CH$_2$), 5.15-5.21 (2H, m, H-4 'ose'), 5.30-5.43 (6H, m, H-1, H-2, H-3 'ose'), 7.41-7.45 (2H, m, Ar), 7.63-7.70 (2H, m, Ar), 7.82-7.95 (4H, m, Ar), 8.76-8.79 (2H, m, β-H), 8.87-8.91 (2H, m, β-H) 9.45-9.49 (2H, m, β-H), 9.59 (2H, s, β-H); $\delta_C$ (125 MHz; CDCl$_3$) 14.25 (CH$_3$), 19.96 (COCH$_3$), 20.61 (COCH$_3$), 20.69 (COCH$_3$), 20.80 (COCH$_3$), 22.85 (CH$_2$), 30.41 (CH$_2$), 32.02 (CH$_2$), 35.84 (CH$_2$), 39.05 (CH$_2$), 62.01 (C-6 'ose'), 68.39 (C-4 'ose'), 71.39 (C-2/3 'ose'), 72.27 (C-5 'ose'), 72.89 (C-2/3 'ose'), 99.24 (C-1 'ose'), 116.52 (Ar), 117.75 (meso-C), 120.68 (meso-C), 122.79 (Ar), 129.95 (Ar), 129.94 (Ar), 143.97 (Ar), 155.45 (Ar), 169.45 (2×COCH$_3$), 170.31 (COCH$_3$), 170.47 (COCH$_3$); (ESI) 1323.5 ([M+H]$^+$ C$_{72}$H$_{83}$N$_4$O$_{20}$$^+$ requires 1323.6).

Example 6

Cell Tests of Selected Compounds in the HT 29 Cell Line

The photosensitizing activity was determined in the human colon adenocarcinoma cell line HT29. The HT29 cell lines were grown in DMEM (cc-pro GmbH) supplemented with 10% heat-inactivated fetal calf serum (FCS, cc-pro GmbH), 1% penicillin (10000 IU) and streptomycin (10000 µg/ml, cc-pro GmbH). Cells were kept as a monolayer culture in a humidified incubator (5% CO$_2$ in air at 37° C.

A photosensitizer stock solution (2 mM) was performed in DMSO and was kept in the dark at 4° C. Further dilution was performed in RPMI 1640 medium without phenol red supplemented with 10% FCS to reach a final photosensitizer concentration of 2 or 10 µM, respectively.

$2·10^4$ cells/ml were seeded in micro plates ($2·10^5$ cells/well). Cells were incubated with fresh medium (RPMI without phenol red) containing 10% FCS with 2 or 10 µM of the photosensitizer for 24 h before light exposure. Before photosensitization, cells were washed, incubated with RPMI without phenol red and 10% FCS, then irradiated at room temperature with a 652 nm diode laser (Ceralas PDT 652, biolitec AG) at a fixed fluence rate of 100 mW/cm$^2$ (50 J/cm$^2$). Following irradiation, cells were incubated in a humidified incubator (5% CO$_2$ in air at 37° C.) for 24 h until cell viability assay.

The cell viability was assessed by the XTT assay. 500 mg XTT (sodium 3'-[phenylaminocarbonyl)-3,4-tetrazolium]-bis(4-methoxy-6-nitro)benzene sulfonic acid, Applichem GmbH) is dissolved in 500 ml PBS-Buffer (without Ca$^{2+}$ and Mg$^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer The solution should be stored frozen and should not be exposed to light. The XTT reagent solution was thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with fresh RPMI without phenol red and 10% FCS (100 µl) prior adding 50 µl XTT reaction solution per well. The micro plate was incubated for 2-3 hours at 37° C. and 5% CO$_2$ until an orange dye is to be formed. The micro plate has been shaken gently to evenly distribute the dye in the wells.

The absorbance of the samples was measured with a spectrophotometer (Bio-Kinetics Reader EL312 e; Bio-Tek Instruments Inc.) at a wavelength of 490 nm. In order to measure reference absorbance (to measure non-specific readings) a wavelength of 630-690 nm was used.

Figure 4A:
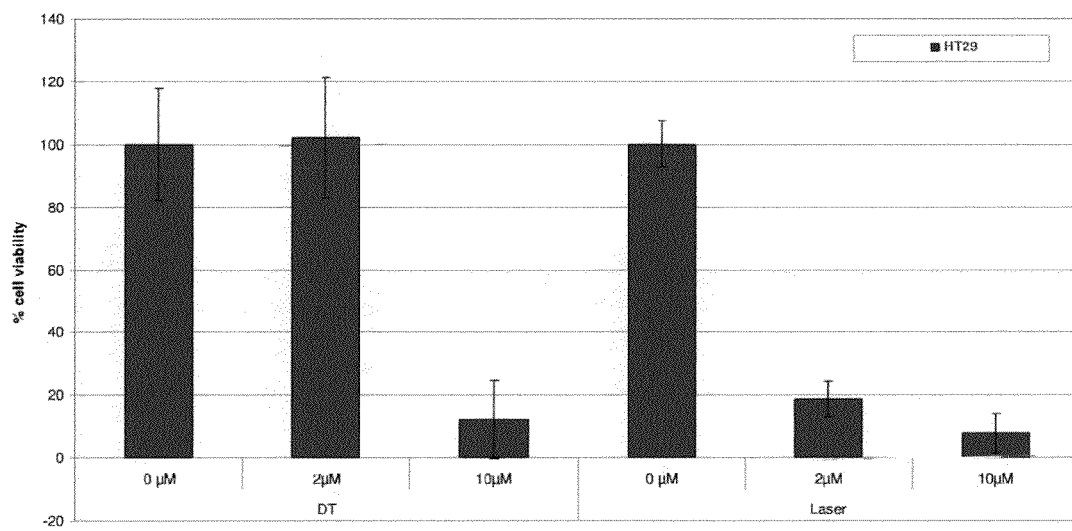
FIG. 4A illustrates the PDT activity of 5,15-bis-(4-carboxyphenyl)-10,20-dihexyl-7,8-dihydroxy-7,8-chlorin in HT 29 cell line (DT: dark toxicity; Laser: photo toxicity).
Figure 4B:
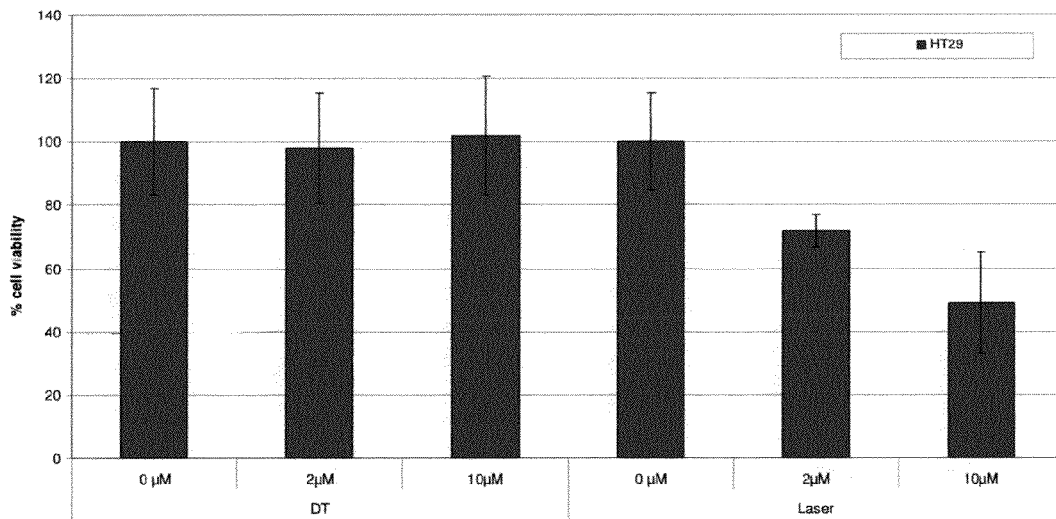
FIG. 4B illustrates the PDT activity of 5,20-bis-(4-carboxyphenyl)-10,15-dihexyl-7,8-dihydroxy-7,8-chlorin in HT 29 cell line (DT: dark toxicity; Laser: photo toxicity).
Figure 4C:
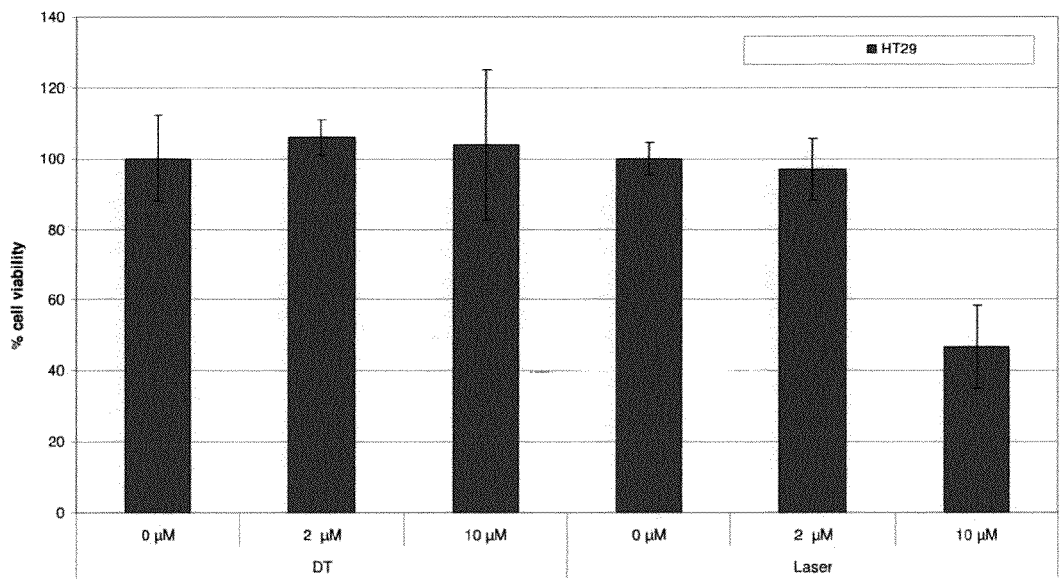
FIG. 4C illustrates the PDT activity of 5,10-bis-(4-carboxyphenyl)-15,20-dihexyl-porphyrin in HT 29 cell line (DT: dark toxicity; Laser: photo toxicity).

FIGS. 4A to 4C illustrate the photodynamic activity (DT means dark toxicity and Laser means photo toxicity) of photosensitizers having a substitution pattern as referred to in the present invention. The three photosensitizers have an $A_2B_2$-substitution pattern of the meso-substituents, combining two polar and two nonpolar meso-substituents. Especially 5,15-bis-(4-carboxyphenyl)-10,20-dihexyl-7,8-dihydroxy-7,8-chlorin exhibits a very strong photodynamic activity in the HT29 cell line, which is known to be very resistant against cell-toxic agents and PDT as well.

Figure 4D:
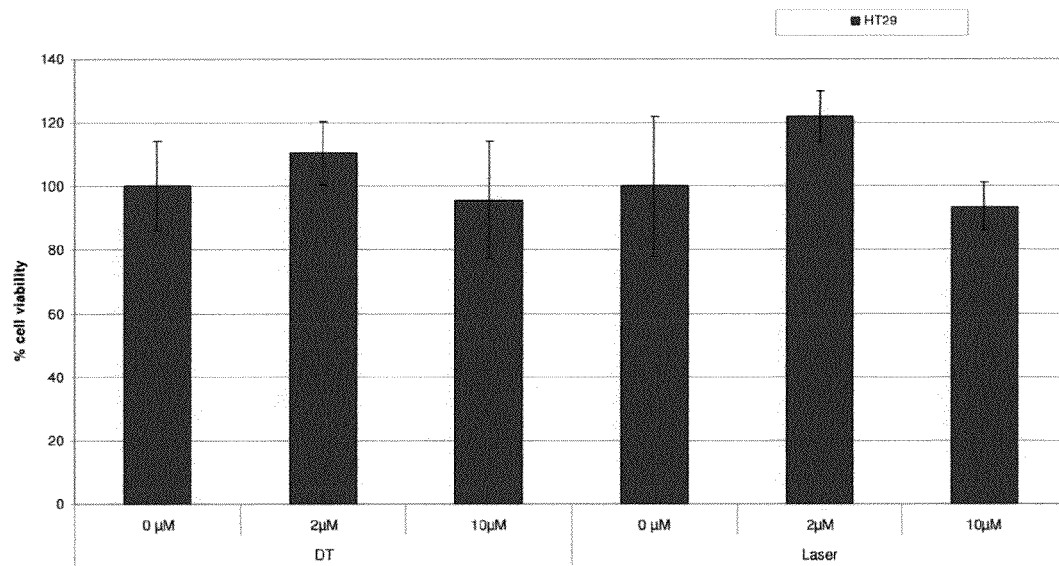
FIG. 4D illustrates the PDT activity of 5-(4-carboxyphenyl)-10,15,20-trihexyl-7,8-dihydroxy-7,8-chlorin in HT 29 cell line (DT: dark toxicity; Laser: photo toxicity).
Figure 4E:
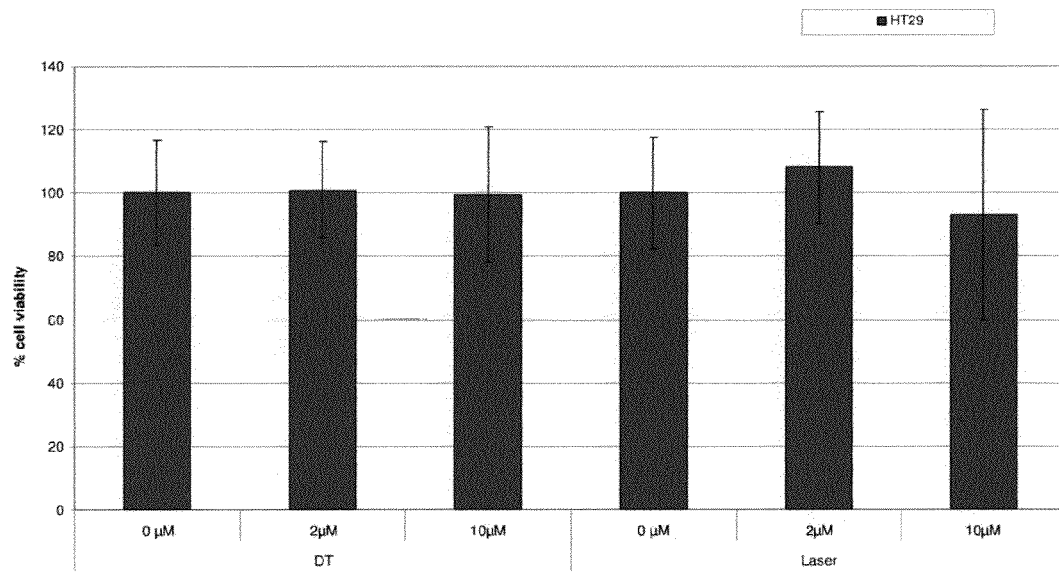
FIG. 4E illustrates the PDT activity of 5-(4-carboxyphenyl)-10,15,20-trihexyl-17,18-dihydroxy-17,18-chlorin in HT 29 cell line (DT: dark toxicity; Laser: photo toxicity).
Figure 4F:
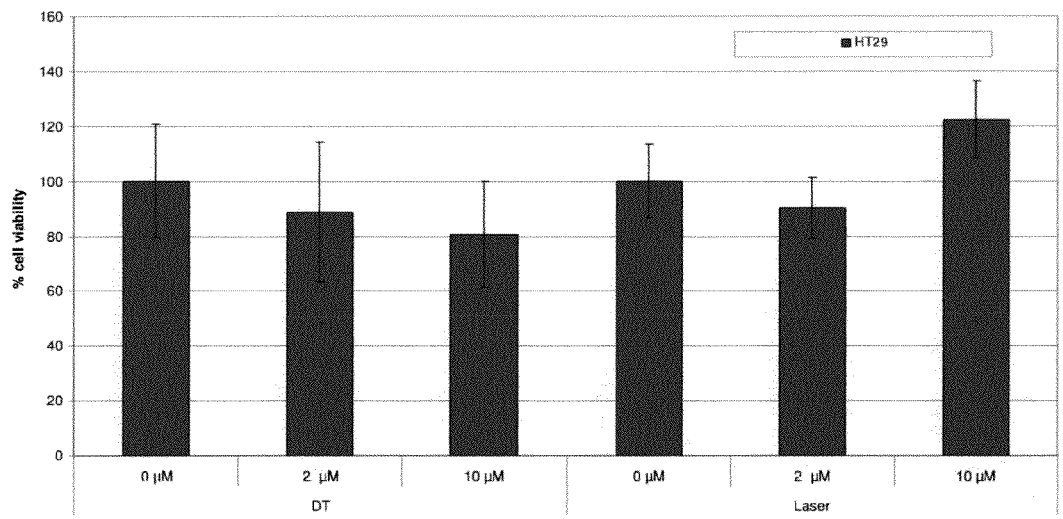
FIG. 4F illustrates the PDT activity of 5,10,15-trihexyl-7,8-dihydroxy-20-(4-methoxycarbonyl-phenyl)-7,8-chlorin in HT 29 cell line (DT: dark toxicity; Laser: photo toxicity).

FIGS. 4D to 4F are included to illustrate, that chlorin photosensitizers which do not have a substitution pattern as referred to in the present invention do not exhibit a promising photodynamic activity in the cell experiments. The three photosensitizers in this case are based on an $A_3B$-substitution pattern of the meso-substituents. In fact, in FIG. 4F, where there are three hexyl chains and one benzoic ester group at the meso-positions the cell viability seems to increase (!) under irradiation (for a photosensitizer concentration of 10 μM, cf. below).

Example 7

Cell Tests of Selected Compounds in a Rabbit Synoviocyte and a Mouse Macrophage Cell Line, HIG82 and J774A.1

The mouse monocytes-macrophages cell line J774A.1 and the rabbit synoviocyte cell line HIG-82 were grown in DMEM (cc-pro GmbH) supplemented with 10% heat-inactivated fetal calf serum (FCS, cc-pro GmbH), 1% penicillin (10000 IU) and streptomycin (10 000 μg/ml, cc-pro GmbH). Cells were kept as a monolayer culture in a humidified incubator (5% $CO_2$ in air at 37° C.).

A photosensitizer stock solution (2 mM) was performed in DMSO and was kept in the dark at 4° C. Further dilution was performed in RPMI 1640 medium without phenol red supplemented with 10% FCS to reach a final photosensitizer concentration of 2 or 10 μM, respectively.

$2 \cdot 10^4$ cells/ml were seeded in micro plates ($2 \cdot 10^5$ cells/well). Cells were incubated with fresh medium (RPMI without phenol red) containing 10% FCS with 2 or 10 μM of the photosensitizer for 24 h before light exposure. Before photosensitization, cells were washed, incubated with RPMI without phenol red and 10% FCS, then irridiated at room temperature with a 652 nm diode laser (Ceralas PDT 652, biolitec AG) at a fixed fluence rate of 100 mW/cm$^2$ (50 J/cm$^2$). Following irradiation, cells were incubated in a humidified incubator (5% $CO_2$ in air at 37° C.) for 24 h until cell viability assay.

The cell viability was assessed by the XTT assay. 500 mg XTT (sodium 3'-[phenylaminocarbonyl)-3,4-tetrazolium]-bis(4-methoxy-6-nitro)benzene sulfonic acid, Applichem GmbH) is dissolved in 500 ml PBS-Buffer (without $Ca^{2+}$ and $Mg^2$) and sterile filtered. Solution was stored in the dark at −20° C. until use. A sterile solution containing PMS (N-methyl dibenzopyrazine methyl sulfate, Applichem GmbH) was needed as an activation reagent for the XTT. 0.383 mg PMS was dissolved in 1 ml PBS-Buffer The solution should be stored frozen and should not be exposed to light. The XTT reagent solution should be thawed in a 37° C. water bath and the activation solution (PMS) was added immediately prior to use. To prepare a reaction solution sufficient for one micro plate (96 wells), 0.1 ml activation solution (PMS) was given to 5 ml XTT reagent. The medium in the micro plate was exchanged with fresh RPMI without phenol red and 10% FCS (100 μl) prior adding 50 μl XTT reaction solution per well. The micro plate was incubated for 2-3 hours at 37° C. and 5% $CO_2$ until an orange dye is to be formed. The micro plate has been shaken gently to evenly distribute the dye in the wells.

The absorbance of the samples was measured with a spectrophotometer (Bio-Kinetics Reader EL312 e; Bio-Tek Instruments Inc.) at a wavelength of 490 nm. In order to measure reference absorbance (to measure non-specific readings) a wavelength of 630-690 nm was used.

FIGS. 5A to 5D illustrate the photodynamic activity of photosensitizers having a substitution pattern as referred to in the present invention against synoviocytes and macrophages, cell types which are especially relevant for the treatment of arthritis and similar inflammatory diseases. The four photosensitizers have the $A_2B_2$-substitution pattern of the meso-substituents, combining two polar and two nonpolar meso-substituents. Especially, 5,15-bis-(4-carboxyphenyl)-10,20-dihexyl-7,8-dihydroxy-7,8-chlorin and 5,20-bis-(4-carboxyphenyl)-10,15-dihexyl-7,8-dihydroxy-7,8-chlorin exhibit a very strong photodynamic activity in the two cell lines.

Figure 5A:
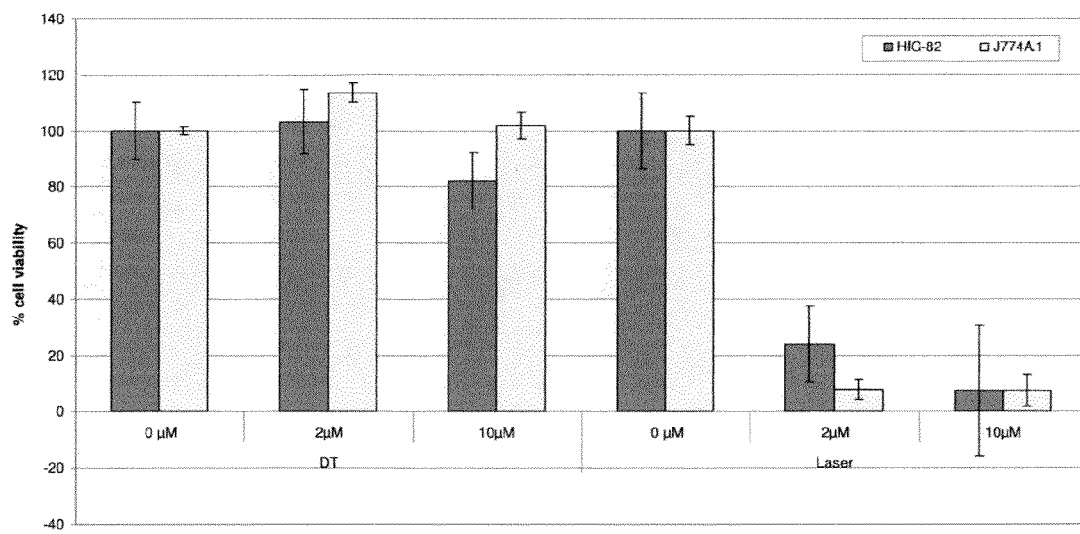
FIG. 5A illustrates the PDT activity of 5,15-bis-(4-carboxyphenyl)-10,20-dihexyl-7,8-dihydroxy-7,8-chlorin in HIG82 and J774A cell lines (DT: dark toxicity; Laser: photo toxicity).
Figure 5B:
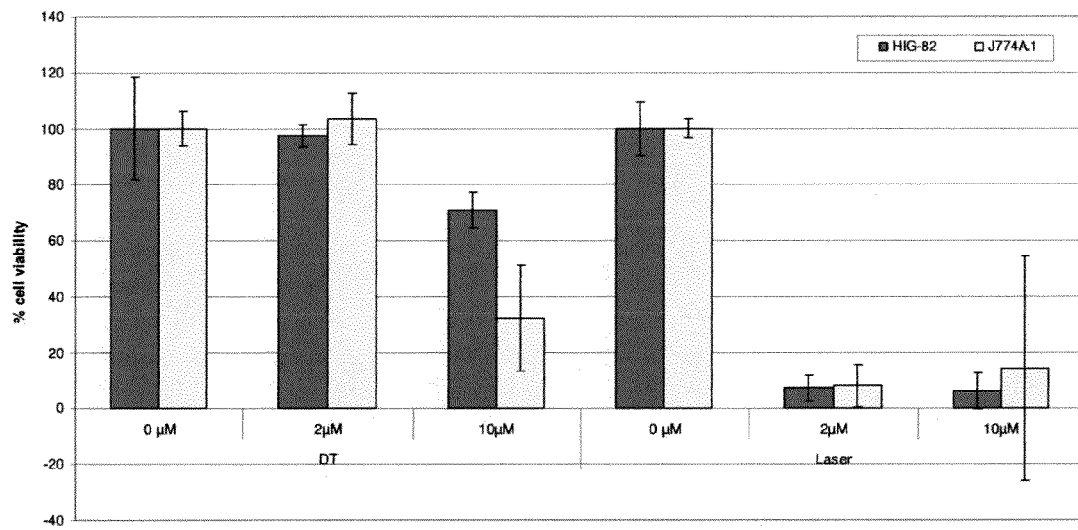
FIG. 5B illustrates the PDT activity of 5,20-bis-(4-carboxyphenyl)-10,15-dihexyl-7,8-dihydroxy-7,8-chlorin in HIG82 and J774A cell lines (DT: dark toxicity; Laser: photo toxicity).
Figure 5C:
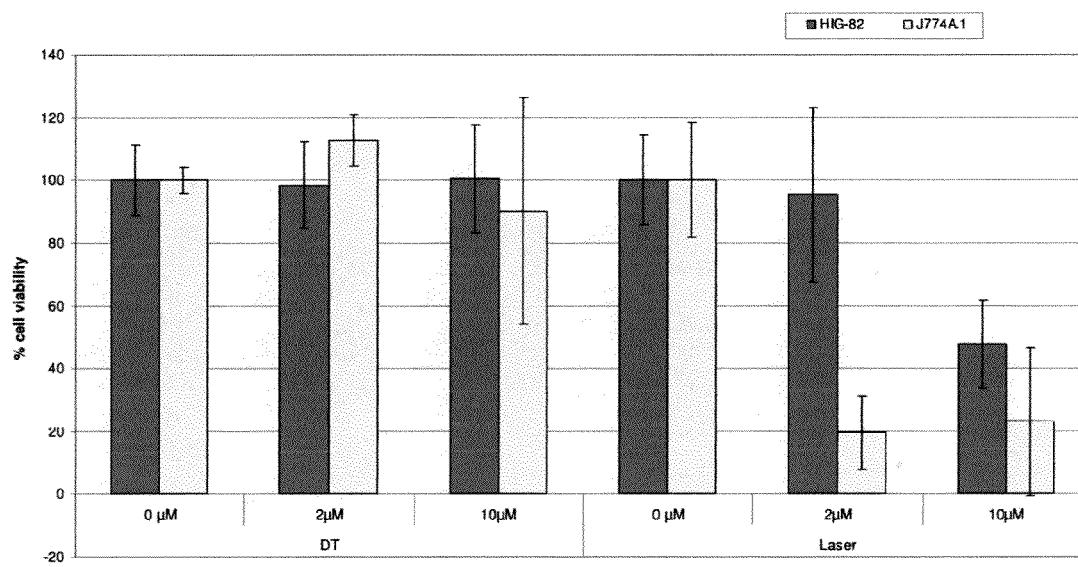
FIG. 5C illustrates the PDT activity of, 8-dihydroxy-5,10-bis-(3-hydroxyphenyl)-15,20-bis-(tridecyl)-7,8-chlorin in HIG82 and J774A cell lines (DT: dark toxicity; Laser: photo toxicity).
Figure 5D:
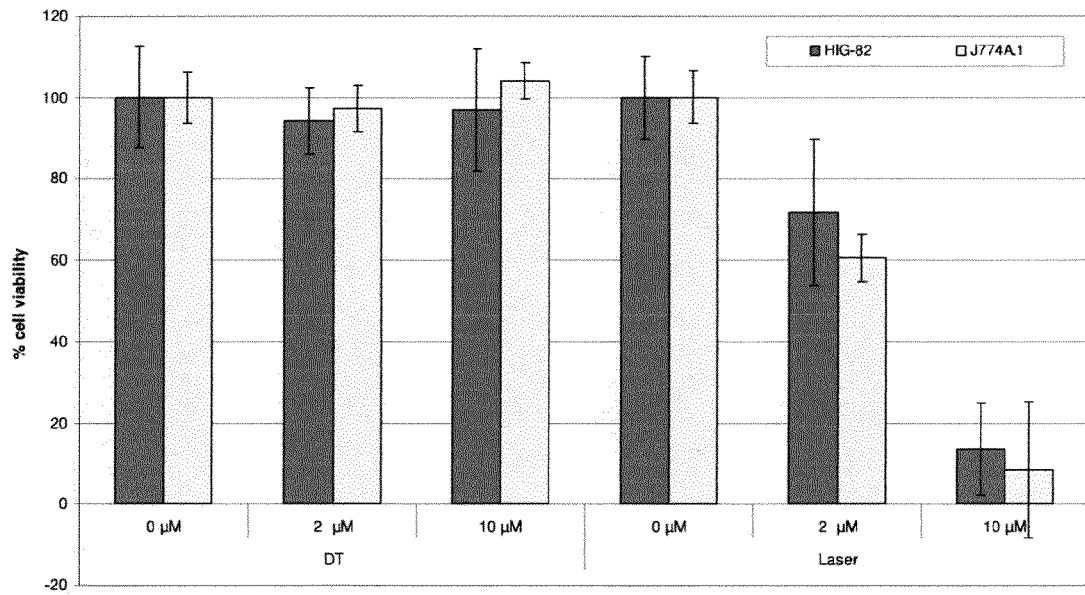
FIG. 5D illustrates the PDT activity of 5,10-bis-(4-carboxyphenyl)-15,20-dihexyl-porphyrin in HIG82 and J774A cell lines (DT: dark toxicity; Laser: photo toxicity).
Figure 5E:
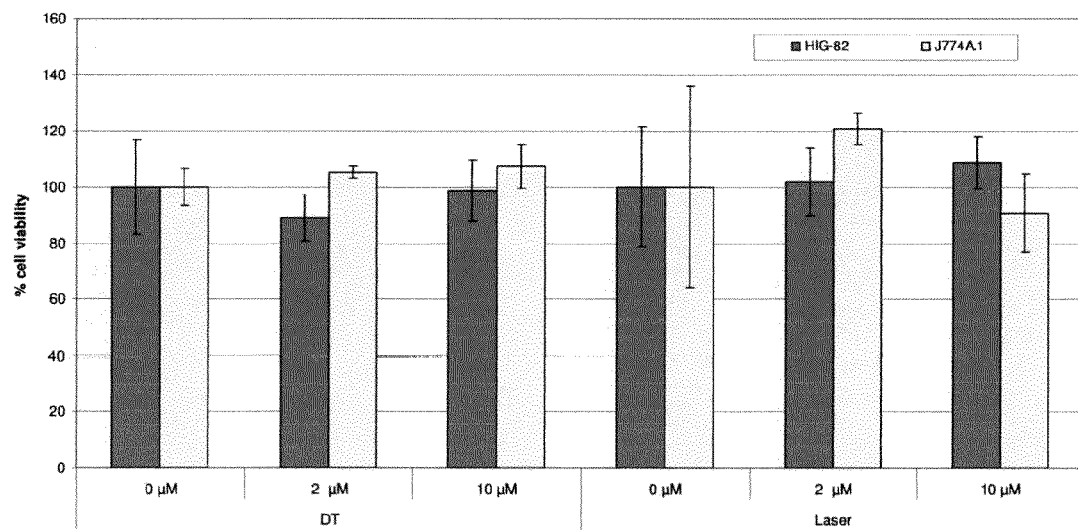
FIG. 5E illustrates the PDT activity of 5,10,15-trihexyl-7,8-dihydroxy-20-(4-methoxycarbonyl-phenyl)-7,8-chlorin in HIG82 and J774A cell lines (DT: dark toxicity; Laser: photo toxicity).

FIG. 5E is again included to illustrate, that chlorin photosensitizers which do not have a substitution pattern as referred to in the present invention do not exhibit a promising photodynamic activity.

Example 8

Cell testing of a liposomal formulation of 5,15-bis-(4-carboxyphenyl)-10,20-dihexyl-7,8-dihydroxy-7,8-chlorin The liposomal formulation of the photosensitizer 5,15-bis-(4-carboxyphenyl)-10,20-dihexyl-7,8-dihydroxy-7,8-chlorin was prepared in analogy to the procedure described in the U.S. Pat. No. 7,354,599 B2 by V. Albrecht, A. Fahr et al.

FIGS. 6A and 6B of the tests with the liposomal formulation illustrate that the photosensitizers of the present invention may be formulated into liposomes for the purpose of e.g. a PDT or arthritis treatment without losing their photodynamic activity. The liposomal formulation of the photosensitizer can be used to e.g. influence the pharmacokinetics of photosensitizer absorption and distribution and increase the bioavailability.

Having described preferred embodiments of the invention with reference to the accompanying examples, it is to be understood that the invention is not limited to the precise embodiments, and that various changes and modifications may be effected therein by skilled in the art without departing from the scope of the invention as defined in the appended claims.

What is claimed is:

1. An unsymmetrically meso-substituted tetrapyrrolic compound comprising two polar and two nonpolar meso-substituents based specifically on the formulas 1, 2, 3 or 4:

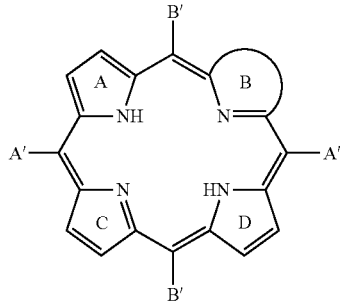

1

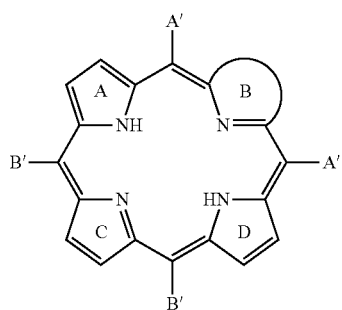

2

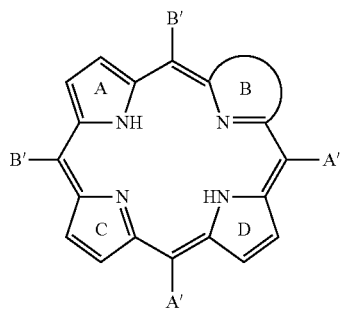

3

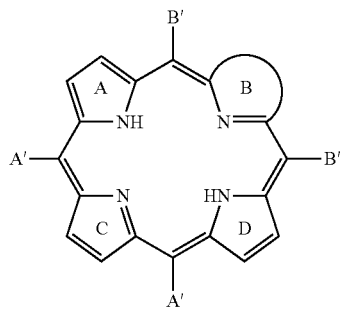

4 wherein the meso-substituents have an A'$_2$B'$_2$-substitution pattern;
wherein B is selected from the group consisting of:

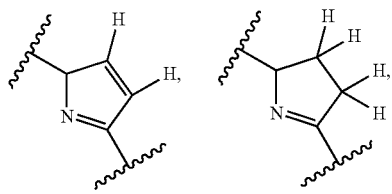

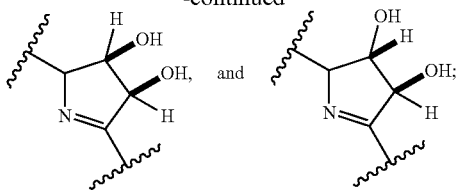

wherein A' is a substituted or unsubstituted alkyl groups or fluoroalkyl groups consisting of 4-15 carbon atoms; and
wherein B' is a phenyl group having the formula:

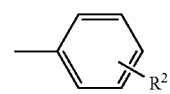

wherein $R^2$ is a substituent either in the meta- or para-position of the phenyl ring and $R^2$ is selected from the group consisting of OH, COOH, COOX, and CO—Y—NH$_2$,
where X is a polyethylene glycol residue with $(CH_2CH_2O)_nCH_3$ with n=1-30 or a carbohydrate moiety, and Y is a peptide or oligopeptide wherein n=1-30.

2. The tetrapyrrolic compound according to claim 1

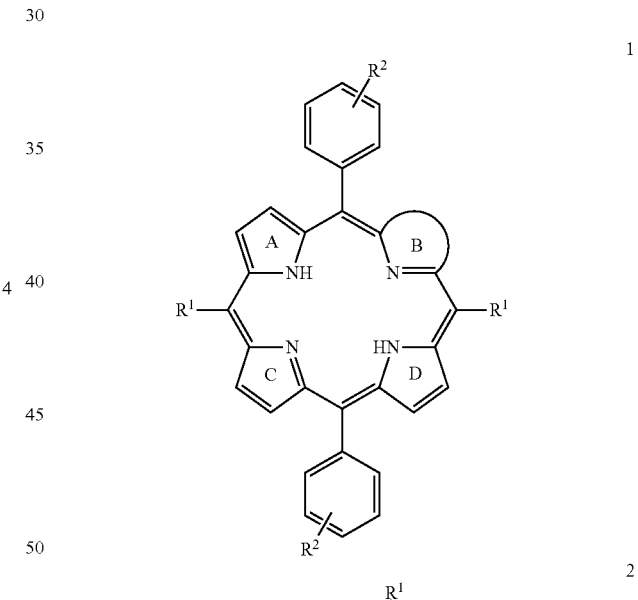

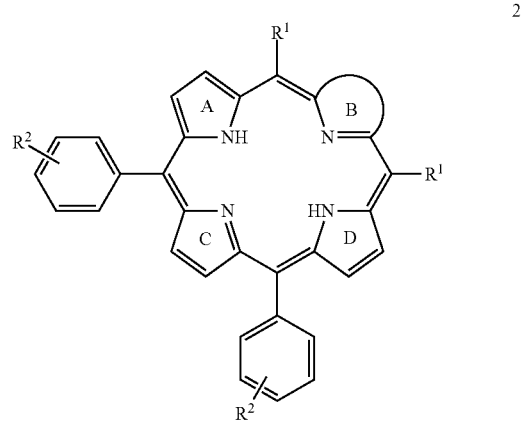

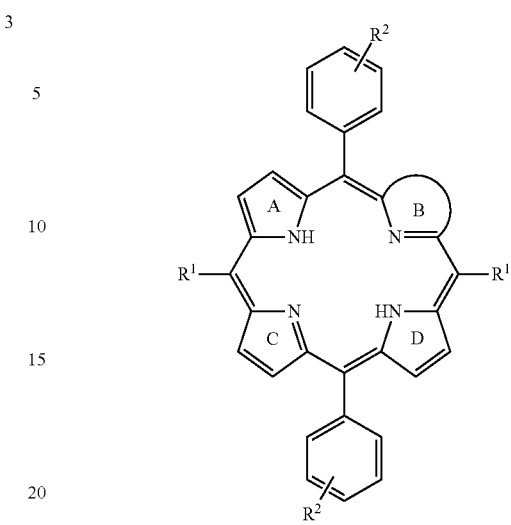

wherein R¹ is A' and A' is as defined in claim 1, and B and R² are as defined in claim 1.

4. The tetrapyrrolic compound according to claim 2, based on formula 1:

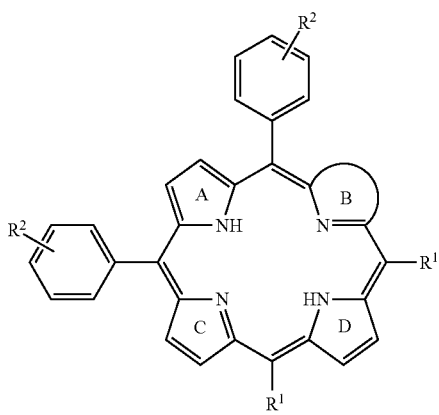

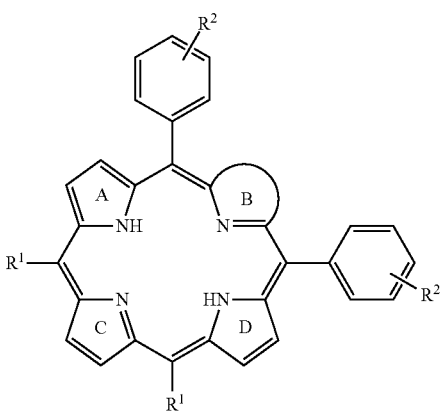

Wherein:
B is selected from the group consisting of:

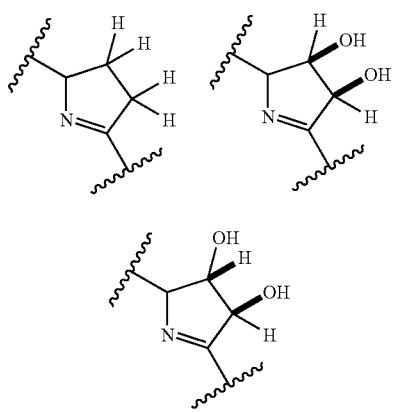

3. The tetrapyrrolic compound according to claim 1 specifically based on formula 1:

Wherein:
B is defined as in claim 2, or a pharmaceutically acceptable derivative thereof.

5. A method of photodynamic therapy comprising administering to a patient a predetermined amount of a compound of claim 1 or a pharmaceutically acceptable derivative thereof, pausing a predetermined time and exposing said patient to light of a predetermined intensity and wavelength.

6. A method for diagnosing or treating arthritis or inflammatory diseases comprising administering to a patient an effective amount of the compound of claim 1 or a pharmaceutically acceptable derivative thereof.

7. A pharmaceutical composition comprising a compound according to claim 1 or a pharmaceutically acceptable derivative thereof as an active ingredient.

8. The pharmaceutical composition according to claim 7 wherein said compound or said pharmaceutically acceptable derivative thereof is conjugated to a targeting agent.

9. The pharmaceutical composition according to claim 8 in which said targeting agent is selected from a group consisting of an antibody, a fragment of an antibody and a peptide.

10. The pharmaceutical composition according to claim 7 in which said pharmaceutical composition is a liposomal formulation.

11. The pharmaceutical composition according to claim 8 in which said pharmaceutical composition is a liposomal formulation.

12. A method of producing compounds of claim 1, wherein substituents on a parent porphyrin (tetrapyrrole) are preselected to direct reduction or dihydroxylation to form a certain isomer of a corresponding chlorin, and wherein in an intermediate step an osmate(VI) ester is reductively cleaved without use of gaseous $H_2S$.

13. The method of production according to claim 12, wherein said substituents are selected by their steric and/or electronic influence to direct dihydroxylation or reduction with diimine to a favored isomer.

14. The tetrapyrrolic compound according to claim 1 wherein B is porphyrin.

15. The tetrapyrrolic compound according to claim 2 specifically based on formula 1.

16. The tetrapyrrolic compound according to claim 1 selected from the group consisting of 5,15-dihexyl-10,20-bis-(4-methoxyphenyl)-porphyrin; 5,10-dihexyl-15,20-bis-(4-methoxyphenyl)-porphyrin; 5,15-dihexyl-10,20-bis-(4-methoxycarbonylphenyl)-porphyrin; 5,15-bis-(3-methoxyphenyl)-10,20-bis-(tridecyl)-porphyrin; 5,10-bis-(3-hydroxyphenyl)-15,20-bis-(tridecyl)-porphyrin; 5,15-bis-(4-carboxyphenyl)-10,20-dihexyl-porphyrin; and 5,10-bis-(4-carboxyphenyl)-15,20-dihexyl-porphyrin.

17. The tetrapyrrolic compound according to claim 2 selected from the group consisting of 5,15-dihexyl-7,8-dihydroxy-10,20-bis-(4-methoxy-carbonylphenyl)-7,8-chlorin; 5,10-dihexyl-7,8-dihydroxy-15,20-bis-(4-methoxy-carbonylphenyl)-7,8-chlorin; 5,20-dihexyl-7,8-dihydroxy-10,15-bis-(4-methoxy-carbonylphenyl)-7,8-chlorin; 5,10-dihexyl-17,18-dihydroxy-15,20-bis-(4-methoxy-carbonylphenyl)-17,18-chlorin; 7,8-dihydroxy-5,15-bis-(3-hydroxyphenyl)-10,20-bis-(tridecyl)-7,8-chlorin; 17,18-dihydroxy-5,15-bis-(3-hydroxyphenyl)-15,20-bis-(tridecyl)-17,18-chlorin; 7,8-dihydroxy-15,20-bis-(3-hydroxyphenyl)-10,15-bis(tridecyl)-7,8-chlorin; 7,8-dihydroxy-5,10-bis-(3-hydroxyphenyl)-15,20-bis-(3-hydroxyphenyl)-7,8-chlorin; 5,15-bis-(4-carboxyphenyl)-10,20-dihexyl-7,8-dihydroxy-7,8-chlorin; and 5,20-bis-(4-carboxyphenyl)-10,15-dihexyl-7,8-dihydroxy-7,8-chlorin.

18. The tetrapyrrolic compound according to claim 1 that is 5,15-bis-(4-carboxyphenyl)-10,20-dihexyl-porphyrin.

* * * * *